(12) United States Patent
Bang-Andersen et al.

(10) Patent No.: US 8,299,095 B2
(45) Date of Patent: Oct. 30, 2012

(54) CRYSTALLINE FORMS OF 4-[2-(4-METHYLPHENYLSULFANYL)-PHENYL] PIPERIDINE WITH COMBINED SEROTONIN AND NOREPINEPHRINE REUPTAKE INHIBITION AND USES THEREOF

(75) Inventors: Benny Bang-Andersen, Copenhagen S (DK); Andre Faldt, Ishoj (DK); Tine Bryan Stensbol, Vaerlose (DK); Silke Miller, Newbury Park, CA (US); Heidi Lopez De Diego, Naerum (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 524 days.

(21) Appl. No.: 12/303,449

(22) PCT Filed: Jun. 15, 2007

(86) PCT No.: PCT/DK2007/050076
§ 371 (c)(1),
(2), (4) Date: Jun. 1, 2009

(87) PCT Pub. No.: WO2007/144006
PCT Pub. Date: Dec. 21, 2007

(65) Prior Publication Data
US 2009/0264465 A1 Oct. 22, 2009

Related U.S. Application Data

(60) Provisional application No. 60/805,009, filed on Jun. 16, 2006.

(30) Foreign Application Priority Data

Jun. 16, 2006 (DK) .................................. 2006 00816
Mar. 20, 2007 (DK) .................................. 2007 00423

(51) Int. Cl.
*A61K 31/451* (2006.01)
*C07D 211/18* (2006.01)
(52) U.S. Cl. ........................................ 514/317; 546/236

(58) Field of Classification Search ................ 514/317; 546/236
See application file for complete search history.

(56) References Cited

U.S. PATENT DOCUMENTS
4,203,980 A * 5/1980 Kompis et al. ................ 514/157
(Continued)

FOREIGN PATENT DOCUMENTS
WO   WO-03029232   4/2003
(Continued)

OTHER PUBLICATIONS
Giron, D. J. Therm. Anal. Cal. 2001, 64, pp. 37-60.*
(Continued)

*Primary Examiner* — Joseph Kosack
*Assistant Examiner* — Matthew Coughlin
(74) *Attorney, Agent, or Firm* — Fish & Richardson P.C.

(57) ABSTRACT

Crystalline forms of 4-[2-(4-methylphenylsulfanyl)-phenyl] piperidine and salts thereof are provided e.g. for the treatment of neuropathic pain.

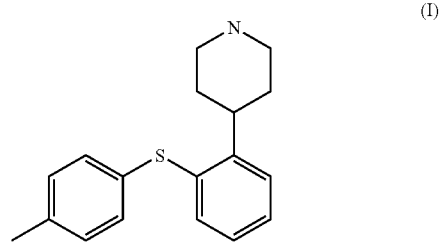

18 Claims, 25 Drawing Sheets

U.S. PATENT DOCUMENTS

Figure 1:
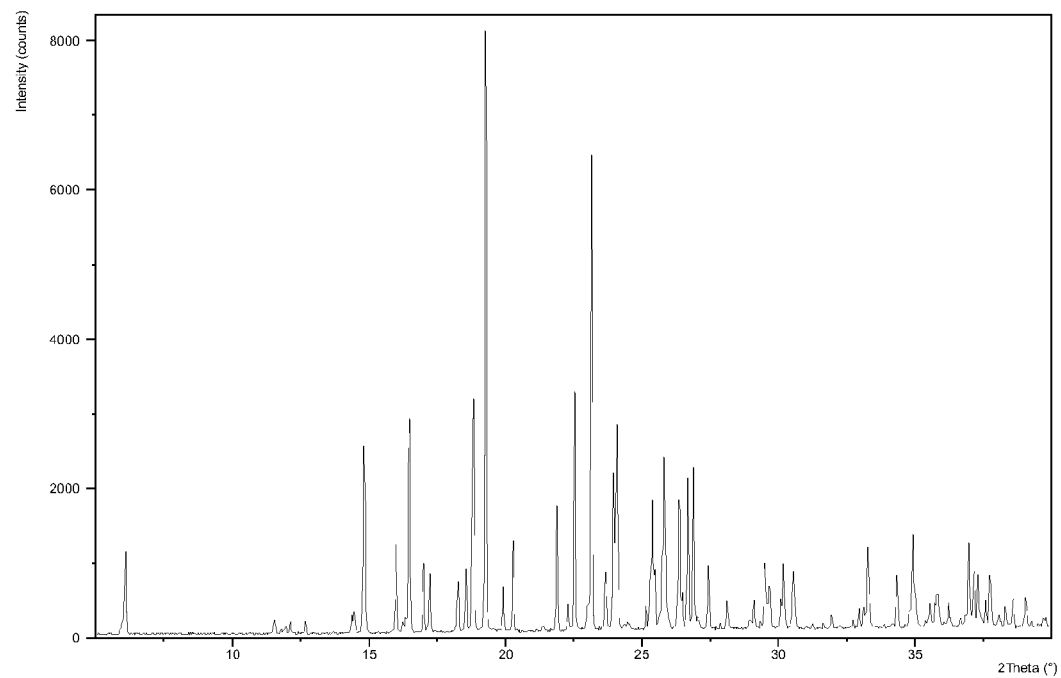

| | | | |
|---|---|---|---|
| 7,053,192 B2 * | 5/2006 | Li et al. ............................ | 536/7.4 |
| 7,148,238 B2 * | 12/2006 | Ruhland et al. ................ | 514/317 |
| 2004/0106655 A1 * | 6/2004 | Kitajima et al. ................ | 514/365 |
| 2005/0043379 A1 * | 2/2005 | Axe et al. ........................ | 514/367 |
| 2005/0107444 A1 * | 5/2005 | Thompsom et al. ............ | 514/345 |
| 2005/0135999 A1 * | 6/2005 | Elomari et al. ................ | 423/706 |
| 2007/0032435 A1 * | 2/2007 | Alani et al. ...................... | 514/18 |
| 2007/0249544 A1 * | 10/2007 | Himmelsbach et al. ......... | 514/27 |
| 2008/0004448 A1 * | 1/2008 | Wayne et al. ................ | 546/276.7 |
| 2008/0089835 A1 * | 4/2008 | Burton ........................... | 423/706 |
| 2008/0103186 A1 * | 5/2008 | Glover et al. .................. | 514/395 |
| 2008/0139569 A1 * | 6/2008 | Rocco et al. ................... | 514/248 |
| 2008/0319024 A1 * | 12/2008 | Greil et al. ..................... | 514/342 |
| 2009/0069281 A1 * | 3/2009 | Austad et al. .................. | 514/183 |
| 2009/0124652 A1 * | 5/2009 | Ach et al. ....................... | 514/293 |
| 2009/0137794 A1 * | 5/2009 | Mendez et al. ................. | 540/78 |
| 2009/0176983 A1 * | 7/2009 | Dova et al. ..................... | 544/242 |
| 2009/0203705 A1 * | 8/2009 | Biagetti et al. ............ | 514/252.02 |
| 2009/0239946 A1 * | 9/2009 | McKeown et al. ............. | 514/494 |
| 2010/0021539 A1 * | 1/2010 | Kowalski et al. .............. | 424/464 |

FOREIGN PATENT DOCUMENTS

| | | |
|---|---|---|
| WO | WO-2004087155 | 10/2004 |
| WO | WO-2006007843 | 1/2006 |

OTHER PUBLICATIONS

Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Schultheiss et al. Crystal Growth & Design 2009, 9, 2950-2967.*

* cited by examiner

Palmitic acid salt 1:1

Adipic acid 1:1 salt (mixture of α and β form)

Glutaric acid 1:1 salt

Malonic acid 1:1 salt, α form

Malonic acid 1:1 salt, β form

Oxalic acid 1:1 salt

Succinic acid 2:1 salt

L-malic acid 1:1 salt, β form

L-aspartic acid 1:1 salt + L-aspartic acid

Glutamic acid 1:1 salt + glutamic acid monohydrate

Citric acid salt 2:1

CRYSTALLINE FORMS OF 4-[2-(4-METHYLPHENYLSULFANYL)-PHENYL] PIPERIDINE WITH COMBINED SEROTONIN AND NOREPINEPHRINE REUPTAKE INHIBITION AND USES THEREOF

CROSS REFERENCE TO PRIOR APPLICATIONS

This is the U.S. National Phase application under 35 U.S.C. §371 of International Patent Application No. PCT/DK2007/050076, filed Jun. 15, 2007, and claims the benefit of Danish Patent Application No. 2006 00816, filed Jun. 16, 2006, U.S. Provisional Application No. 60/805,009, filed Jun. 16, 2006, and Danish Patent Application No. 2007 00423, filed Mar. 20, 2007 all of which are incorporated by reference herein. The International Application published in English on Dec. 21, 2007 as WO 2007/144006 under PCT Article 21(2).

The perception of pain is more complicated than a direct transmission of signals from an injured part of the body to specific receptors in the brain, and wherein the pain perceived is proportional to the injury. Rather, damage to peripheral tissue and injury to nerves may cause alterations in the central neural structures involved in pain perception affecting subsequent pain sensitivity. This neuroplasticity may bring about a central sensitization in response to longer lasting noxious stimuli, which may manifest itself as e.g. chronic pain, i.e. that the perception of pain remains even after the noxious stimulus has stopped, or as hyperalgesia, i.e. an increased response to a stimulus, which is normally painful. On of the more mysterious and dramatic examples of this is the "phantom limb syndrome", i.e. the persistence of pain that existed in a limb prior to its amputation. For a recent review of central neuroplasticity and pain see Melzack et al in *Ann. N.Y. Acad. Sci.*, 933, 157-174, 2001.

Chronic pain, such as neuropathic pain manifests itself differently than other types of pain, e.g. somatic or visceral pain. The pain is often described as shooting, burning, pins and needles, numb or stabbing. Common causes of neuropathic pain include alcoholism, amputation, back, leg and hip problems, chemotherapy, diabetes, HIV, multiple sclerosis, spine surgery, and herpes zoster virus infection.

The central component to chronic pain may explain why chronic pain, such as e.g. neuropathic pain often responds poorly to classical analgesics, such as non-steroid anti-inflammatory drugs (NSAIDS) and opioid analgesics. Tricyclic antidepressants (TCA), typified by amitryline, have become standard for the treatment of neuropathic pain, and the effect is believed to be mediated by the combined inhibitory effect on the serotonin transporter and the norepinephrine transporter [*Clin Ther.*, 26, 951-979, 2004]. More recently, the so-called dual action antidepressants having an inhibitory effect on both the serotonin and the norepinephrine reuptake have been used clinically for the treatment of neuropathic pain [*Human Psychopharm.*, 19, S21-S25, 2004]. Examples of dual acting antidepressants are venlafaxine and duloxetine, and this class of antidepressants is often referred to as SNRI.

Data on the use of selective serotonine reuptake inhibitors (SSRI) for neuropathic pain is scarce, but generally suggest a limited effect [*Bas. Clin. Pharmacol.*, 96, 399-409, 2005]. In fact, it has been hypothesized that SSRI's are only weakly antinociceptive in and of themselves but that inhibition of the serotonin transporter augments the antinociceptive effect of norepinephrine reuptake inhibition. This notion is supported by a review of 22 animal and five human studies showing that SNRI's have superior antinociceptive effect compared to norepinephrine reuptake inhibitors, which again are superior to SSRI [*Pain Med.* 4, 310-316, 2000].

Recent data on the 5-$HT_3$ antagonist odansetron implies that 5-$HT_3$ antagonists may have an analgesic effect and thus be useful in the treatment of neuropathic pain [*Anesth. Analg.*, 97, 1474-1478, 2003].

The use of tricyclic antidepressants is, however, associated with known, anticholinergic side effects, such as e.g. drowsiness, anxiety, restlessness, and cognitive and memory difficulties. Hence, there is a need in the art to find alternative ways of treating neuropathic pain.

The international patent application published as WO 2003/029232 discloses e.g. the compound 4-[2-(4-methylphenylsulfanyl)phenyl]piperidine as a free base and the corresponding HCl salt. The compound is reported to be an inhibitor of the serotonin transporter and the serotonin receptor 2C (5-$HT_{2C}$), and is said to be useful for the treatment of affective disorders, e.g. depression and anxiety.

SUMMARY OF THE INVENTION

The present inventors have surprisingly found that in addition to the already known pharmacological profile, 4-[2-(4-methylphenylsulfanyl)-phenyl]piperidine is a potent inhibitor of the serotonin reuptake and the norepinephrine reuptake, an antagonist of the serotonin receptor 3 (5-$HT_3$), an antagonist of the serotonin receptor 2A (5-$HT_{2A}$), and an inhibitor or the $\alpha_1$ adrenergic receptor, and the compound may as such be useful in treatment of e.g. chronic of pain. Accordingly, the invention relates to compound I, which is 4-[2-(4-methylphenyl-sulfanyl)phenyl]piperidine and pharmaceutically acceptable salts thereof in a crystalline form provided said compound is not 4-[2-(4-methylphenyl-sulfanyl)phenyl]-piperidine hydrochloride addition salt.

In one embodiment, the invention relates to compound I for use in therapy.

In one embodiment, the invention relates to a method of treatment comprising the administration of a therapeutically effective amount of compound I to a patient in need thereof.

In one embodiment, the invention relates to a pharmaceutical composition comprising compound I.

In one embodiment, the invention relates to the use of compound I for the manufacture of a medicament.

FIGURES

FIG. 1: X-ray diffraction pattern of the HBr addition salt of compound I

Figure 2:
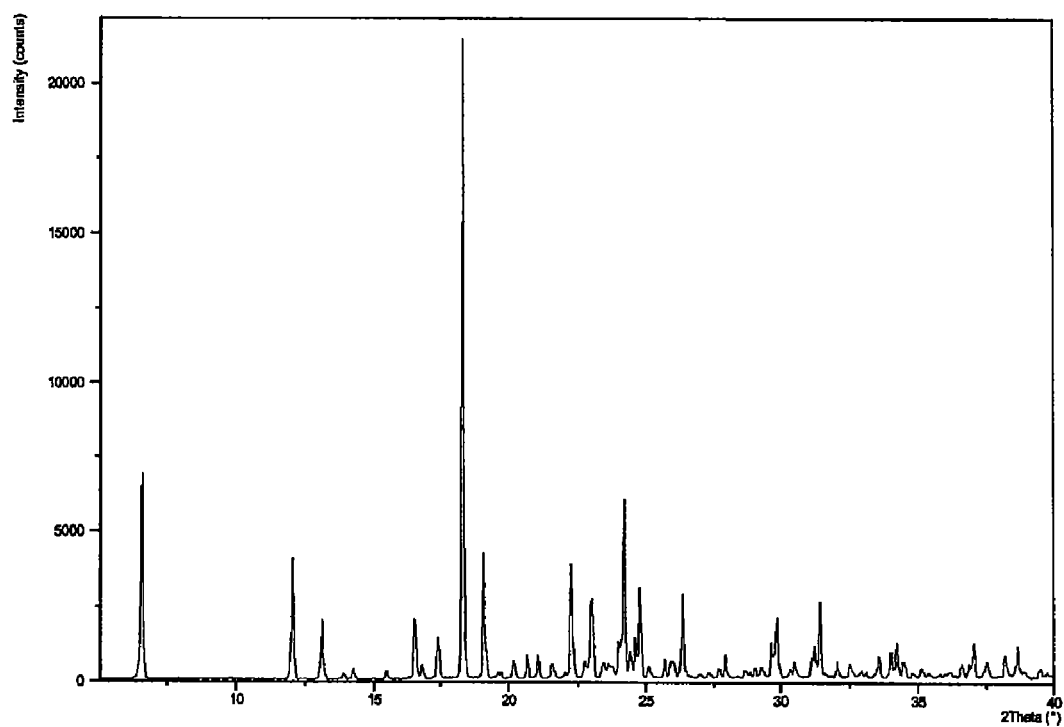
Figure 3:
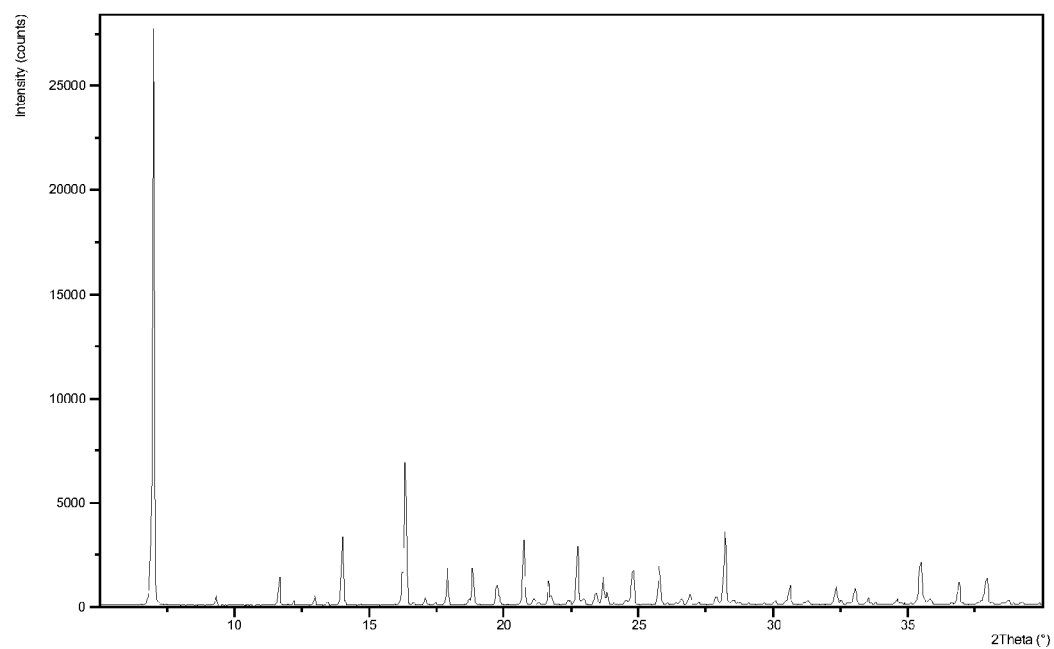

FIG. 2: X-ray diffraction pattern of the HBr addition salt solvate of compound I FIG. 3: X-ray diffraction pattern of the palmitic acid addition salt of compound I FIG. 4: X-ray diffraction pattern of the DL-lactic acid addition salt of compound I FIG. 5: X-ray diffraction pattern of the adipic acid addition salt (1:1) of compound I ($\alpha+\beta$ form)

Figure 6:
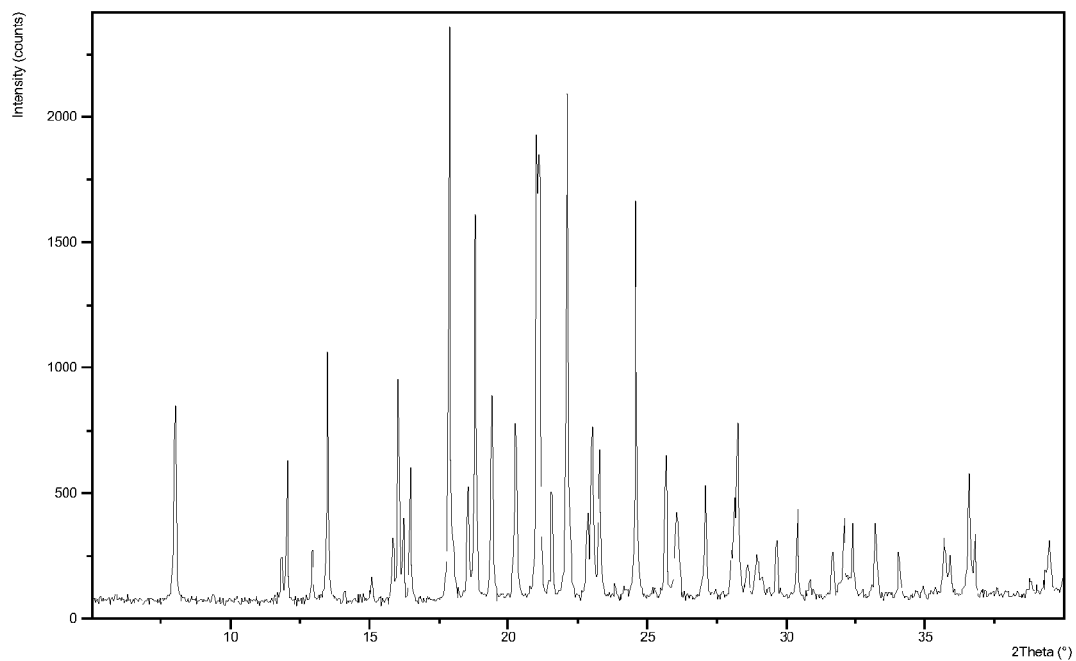
Figure 7:
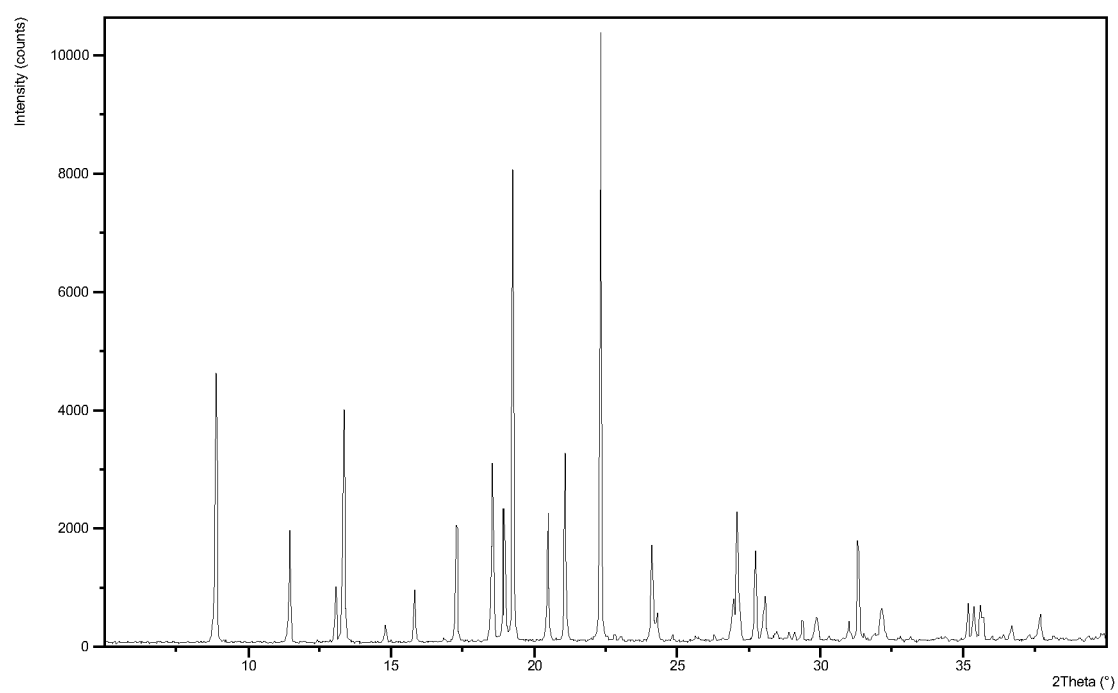
Figure 11:
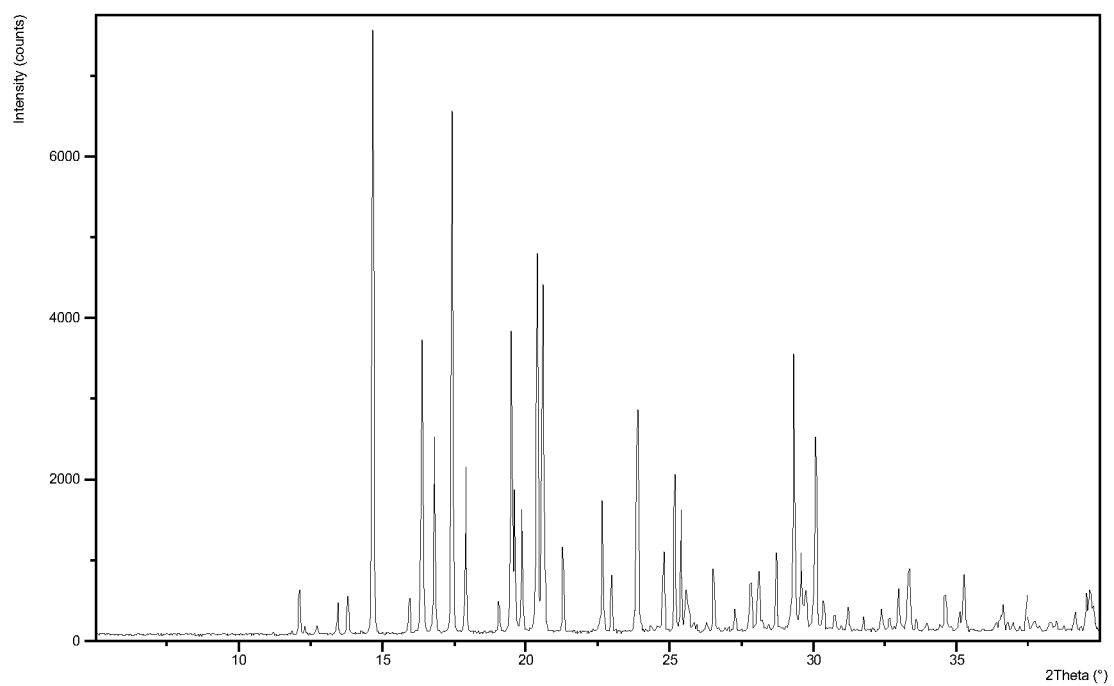
Figure 12:
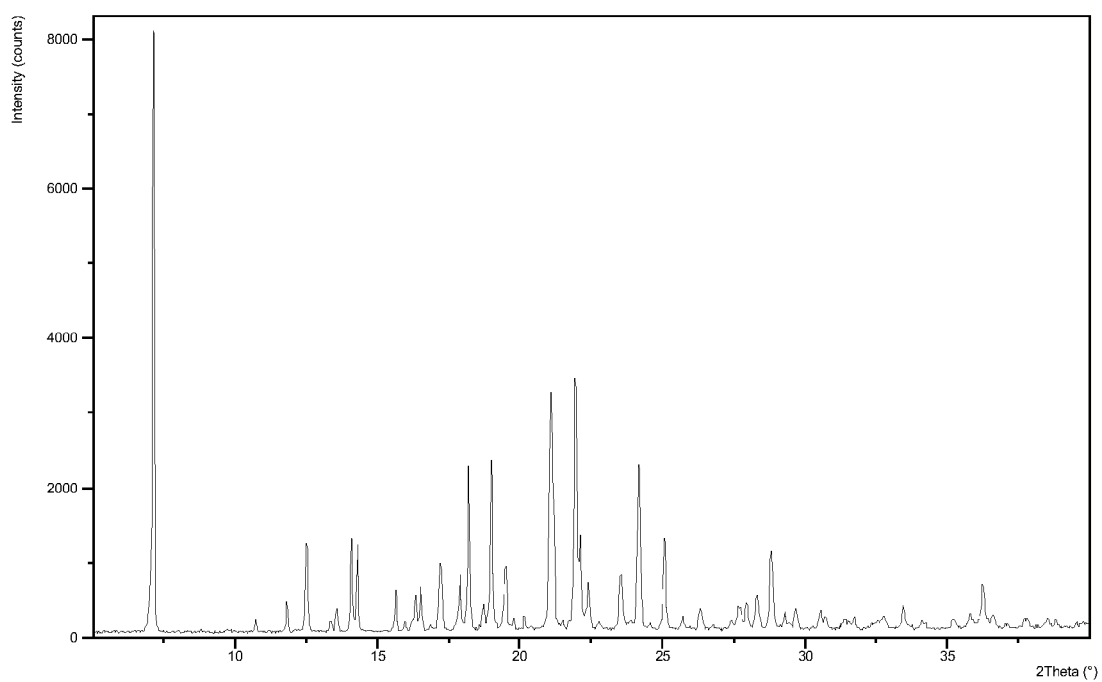
Figure 13:
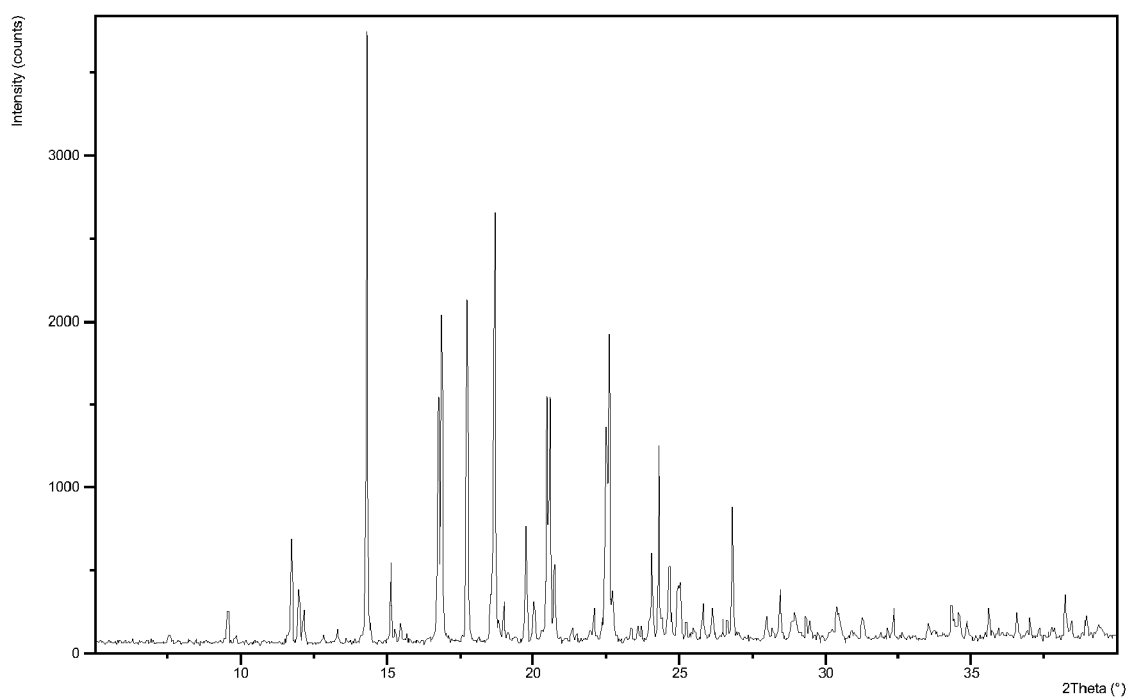
Figure 14:
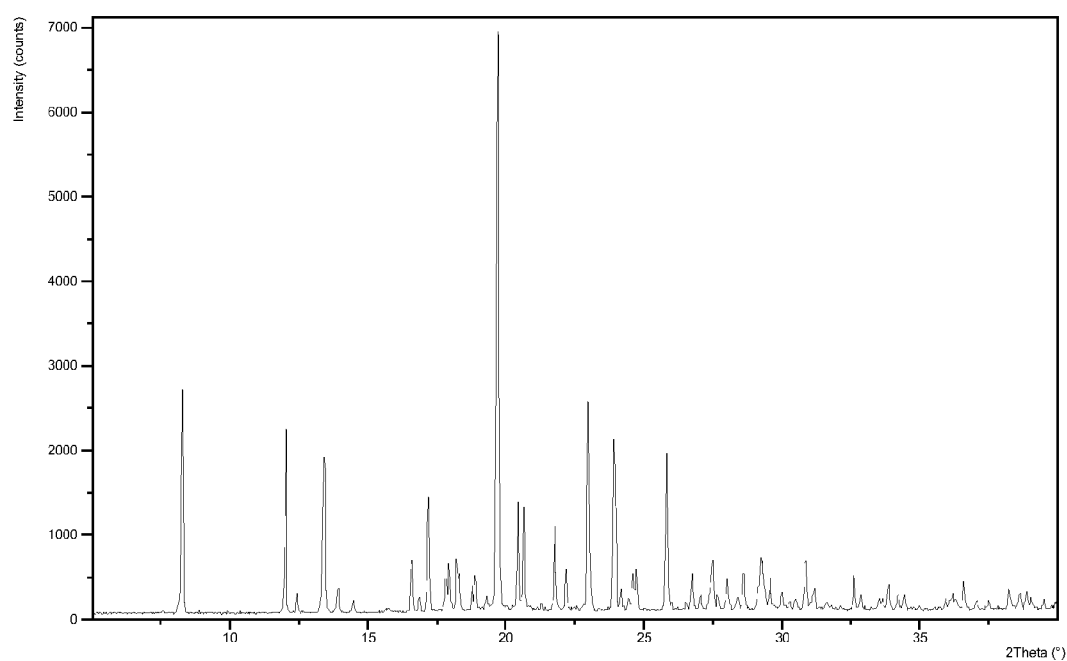
Figure 15:
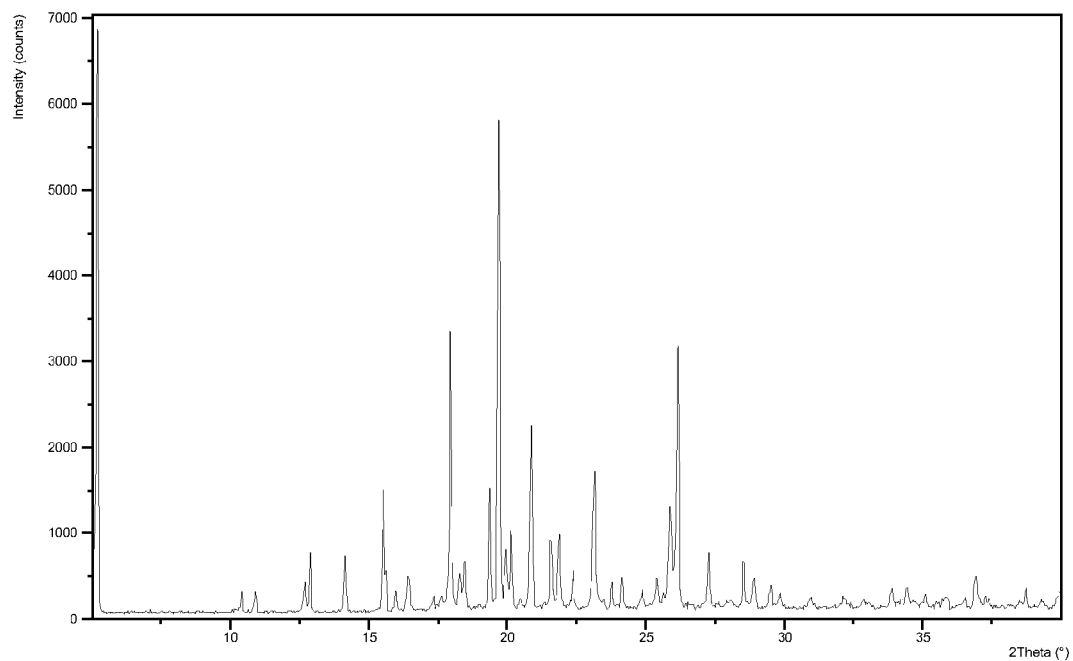
Figure 16:
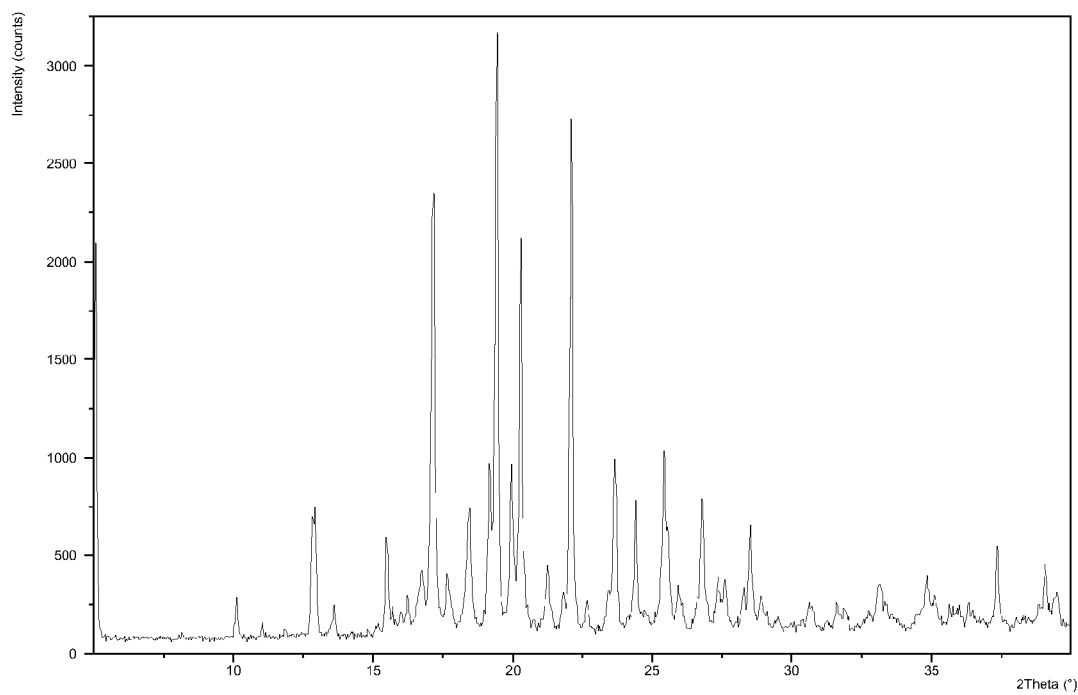
Figure 20:
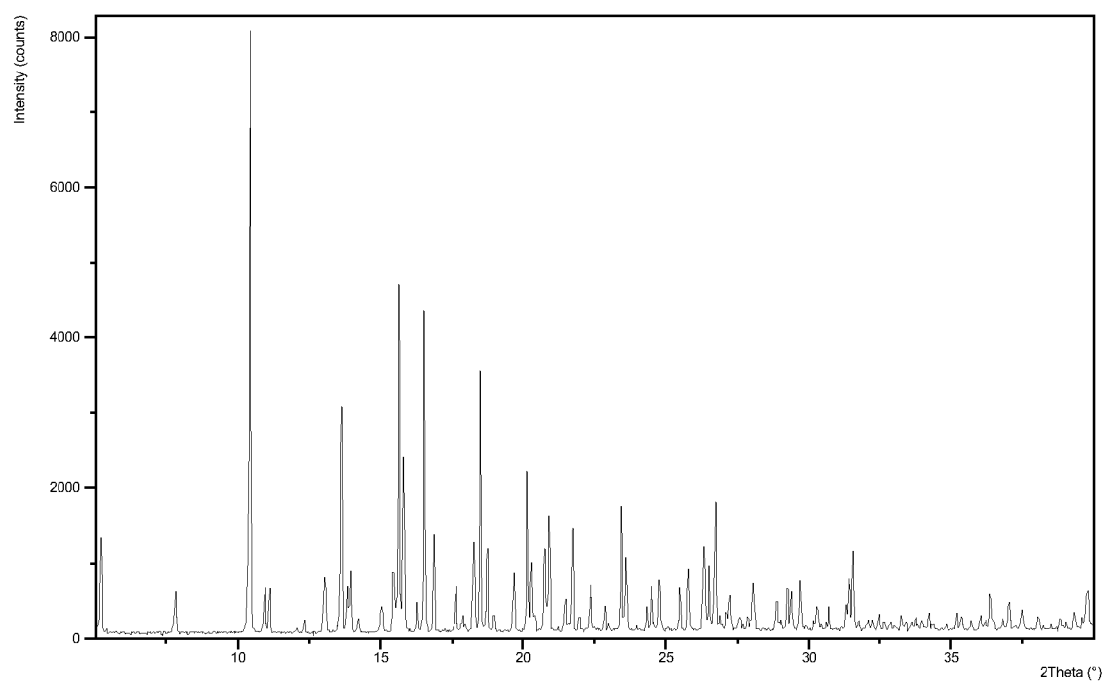
Figure 21:
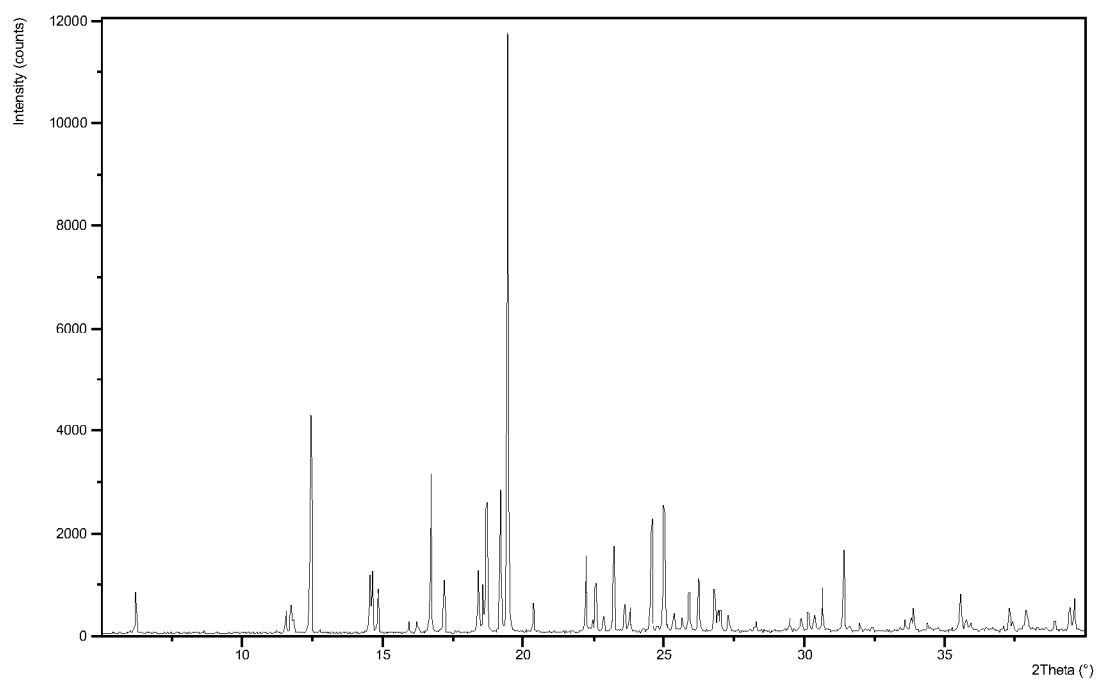
Figure 22:
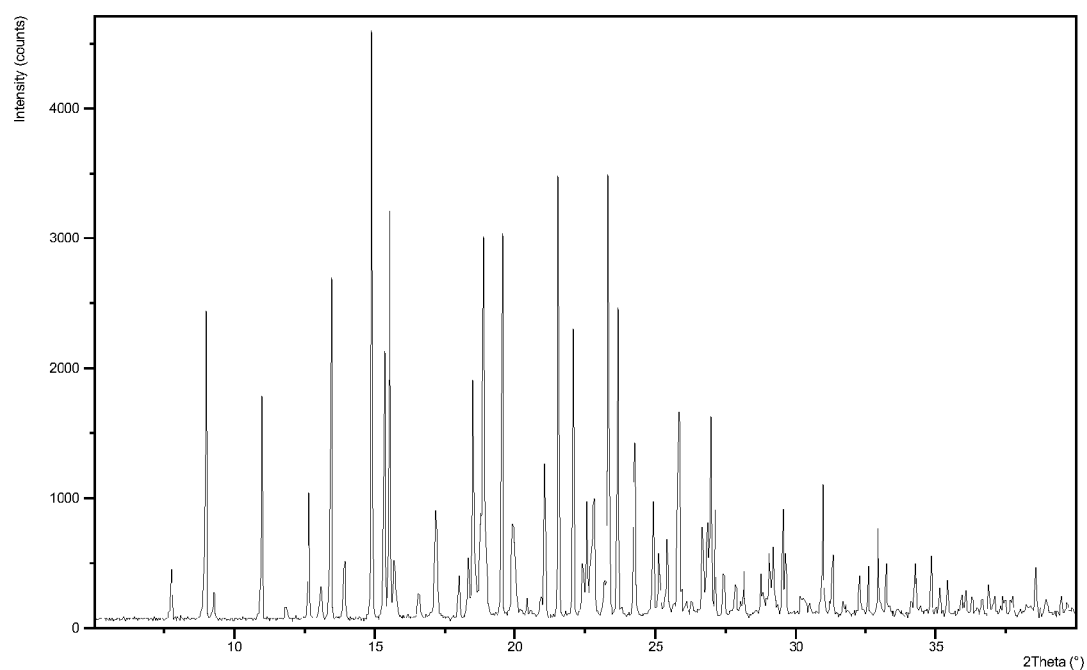

FIG. 6: X-ray diffraction pattern of the adipic acid addition salt (2:1) of compound I FIG. 7: X-ray diffraction pattern of the fumaric acid addition salt (1:1) of compound I FIG. 8: X-ray diffraction pattern of the glutaric acid addition salt (1:1) of compound I FIG. 9: X-ray diffraction pattern of the malonic acid addition salt (1:1) of compound I, $\alpha$-form FIG. 10: X-ray diffraction pattern of the malonic acid addition salt of compound I, $\beta$-form FIG. 11: X-ray diffraction pattern of the oxalic acid addition salt (1:1) of compound I FIG. 12: X-ray diffraction pattern of the sebacoinic acid addition salt (2:1) of compound I FIG. 13: X-ray diffraction pattern of the succinic acid addition salt (2:1) of compound I FIG. 14: X-ray diffraction pattern of the L-malic acid addition salt (1:1) of compound I, α-form FIG. 15: X-ray diffraction pattern of the L-malic acid addition salt (1:1) of compound I, β-form FIG. 16: X-ray diffraction pattern of the D-tartaric acid addition salt (1:1) of compound I FIG. 17: X-ray diffraction pattern of the L-aspartic acid addition salt (1:1) of compound I in mixture with L-aspartic acid FIG. 18: X-ray diffraction pattern of the L-aspartic acid addition salt hydrate (1:1) of compound I in mixture with L-aspartic acid FIG. 19: X-ray diffraction pattern of the glutamic acid addition salt (1:1) of compound I in mixture with glutamic acid monohydrate FIG. 20: X-ray diffraction pattern of the citric acid addition salt (2:1) of compound I FIG. 21: X-ray diffraction pattern of the HCl acid addition salt of compound I FIG. 22: X-ray diffraction pattern of the phosphoric acid addition salt (1:1) of compound I FIG. 23: Dopamine levels in prefrontal cortex upon administration of compounds of the present invention.

Figure 24:
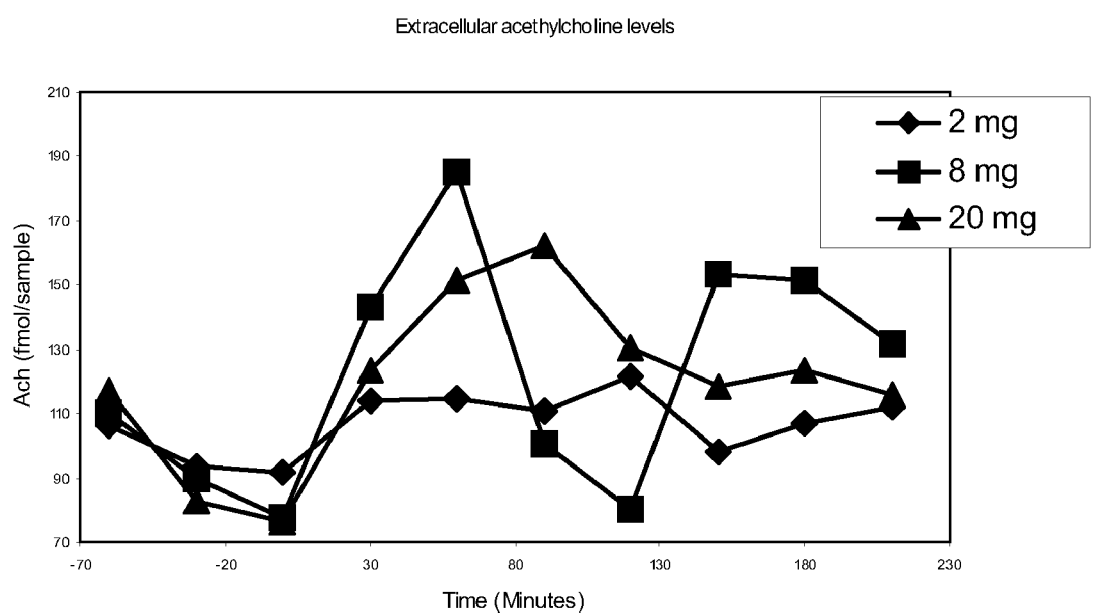

FIG. 24: Acetylcholine levels in prefrontal cortex upon administration of compounds of the present invention.

Figure 25A:
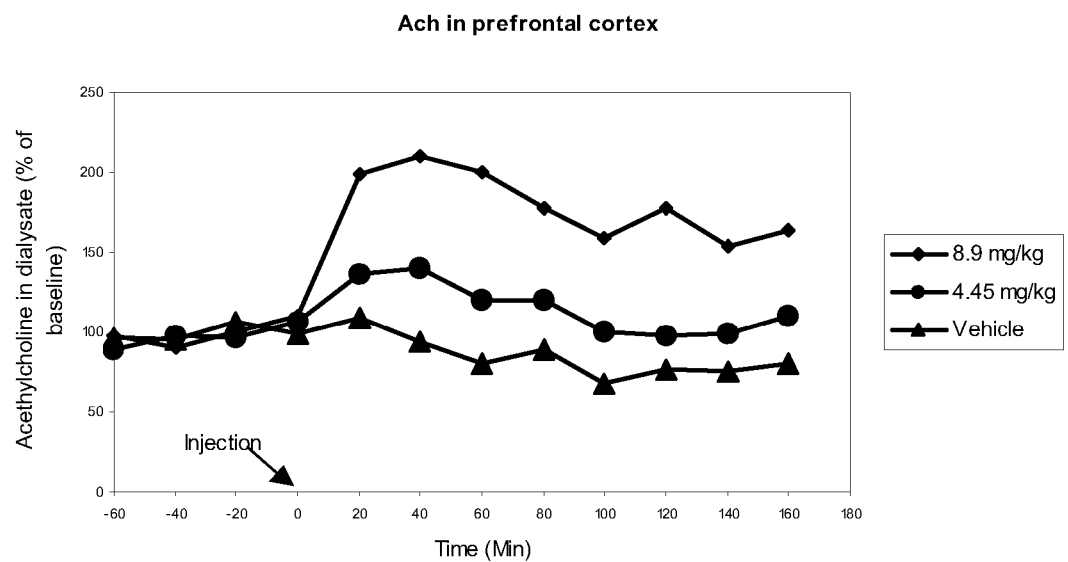

FIGS. 25a and b: Acetylcholine levels in the prefrontal cortex and ventral hippocampus upon administration of compounds of the present invention.

DETAILED DESCRIPTION OF THE INVENTION

The present invention relates to compound I, which is 4-[2-(4-methylphenylsulfanyl)-phenyl]piperidine and pharmaceutically acceptable salts thereof in a crystalline form provided said compound is not the hydrochloride addition salt. The structure of 4-[2-(4-methylphenylsulfanyl)-phenyl]piperidine is

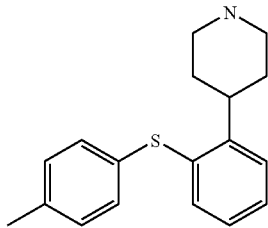

The pharmacological profile of the compounds of the present invention is depicted in the examples, but can be summarised as follows. The compounds are inhibitors of the serotonin and norepinephrine reuptake; they inhibit the serotonin receptors 2A, 2C and 3; and they inhibit the α-1 adrenergic receptor.

In one embodiment, said pharmaceutically acceptable salts are acid addition salts of acids that are non-toxic. Said salts include salts made from organic acids, such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, malonic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic salts, such as hydrobromic, sulfuric, sulfamic, phosphoric and nitric acids. Additional useful salts are listed in the table in example 1d (table 1).

In one embodiment, the compound of the present invention, i.e. the compound of formula I, is the HBr addition salt In one embodiment, the compound of the present invention is the DL-lactic acid addition salt, and in particular the 1:1 salt.

In one embodiment, the compound of the present invention is the L-aspartic acid addition salt, and in particular the 1:1 salt.

In one embodiment, the compound of the present invention is the glutamic acid addition salt, and in particular the 1:1 salt.

In one embodiment, the compound of the present invention is the glutaric acid addition salt, and in particular the 1:1 salt.

In one embodiment, the compound of the present invention is the malonic acid addition salt, and in particular the 1:1 salt that is found to exist in two polymorphic modifications α and β of which the β form is believed to be the most stable based on a lower solubility.

In one embodiment, the compounds of the present invention is in a purified form. The term "purified form" is intended to indicate that the compound is essentially free of other compounds or other forms, i.e. polymorphs of said compound, as the case may be.

Oral dosage forms, and in particular tablets and capsules, are often preferred by the patients and the medical practitioner due to the ease of administration and the consequently better compliance. For tablets and capsules, it is preferable that the active ingredients are crystalline.

Crystals of the present invention may exist as solvates, i.e. crystals wherein solvent molecules form part of the crystal structure. The solvate may be formed from water, in which case the solvates are often referred to as hydrates. Alternatively, the solvates may be formed from other solvents, such as e.g. ethanol, acetone, or ethyl acetate. The exact amount of solvate often depends on the conditions. For instance, hydrates will typically loose water as the temperature is increased or as the relative humidity is decreased. Compounds, which do not change or which change only little when conditions, such as e.g. humidity change are generally regarded as better suited for pharmaceutical formulations. It is noted that the HBr addition salt does not form hydrates when precipitated from water whereas compounds such as the succinate, malate and tartrate acid addition salts do.

Some compounds are hygroscopic, i.e. they absorb water when exposed to humidity. Hygroscopicity is generally regarded as an undesired property for compounds, which are to be presented in a pharmaceutical formulation, in particular in a dry formulation, such as tablets or capsules. In one embodiment, the invention provides crystals with low hygroscopicity.

For oral dosage forms using crystalline active ingredients it is also beneficial if said crystals are well-defined. In the present context, the term "well-defined" in particular means that the stoichiometry is well-defined, i.e. that the ratio between the ions forming the salt is the ratio between small integers, such as 1:1, 1:2, 2:1, 1:1:1, etc. In one embodiment, the compounds of the present invention are well-defined crystals.

The solubility of an active ingredient is also of significance for the choice of dosage form as it may have a direct impact on bio-availability. For oral dosage forms, a higher solubility of the active ingredient is generally believed to be beneficial as it increases the bio-availability. Some patients, e.g. elderly patients may have difficulties swallowing tablets, and oral drop solutions may be a suitable alternative avoiding the need for swallowing tablets. In order to limit the volume of an oral drop solution, it is necessary to have a high concentration of the active ingredient in the solution, which again requires a high solubility of the compound. As shown in table 3, DL-lactic acid, L-aspartic acid, glutamic acid, glutaric acid and malonic acid addition salts have exceptionally high solubility.

Crystal forms impact the filtration and processing properties of a compound. Needle formed crystals tend to be more difficult to handle in a production environment as filtration becomes more difficult and time consuming. The exact crystal form of a given salt may depend e.g. on the conditions under which the salt was precipitated. The HBr acid addition salt of the present invention grows needle-shaped, solvated crystals when precipitated from ethanol, acetic acid and propanol, but crystals of a non-hydrated form, which are not needle-shaped, when HBr addition salt is precipitated from water, providing superior filtration properties.

Table 3 also depicts the Resulting pH, i.e. the pH in the saturated solution of the salt. This property is of importance because moisture can never be completely avoided during storage and the accumulation of moisture will give rise to a pH decrease in or on a tablet comprising a low Resulting pH salt, which may decrease shell life. Moreover, a salt with a low resulting pH may give rise to corrosion of process equipment if tablets are made by wet granulation. The data in table 3 suggest that the HBr, HCl and adipic acid addition salts may be superior in this respect.

In one embodiment, the compound of the present invention is the HBr addition salt in a crystalline form, in particular in a purified form. In a further embodiment, said HBr salt has peaks in an X-ray powder diffractogram (XRPD) at approximately 6.08°, 14.81°, 19.26° and 25.38° 2θ, and in particular said HBr salt has an XRPD as depicted in FIG. 1.

Figure 4:
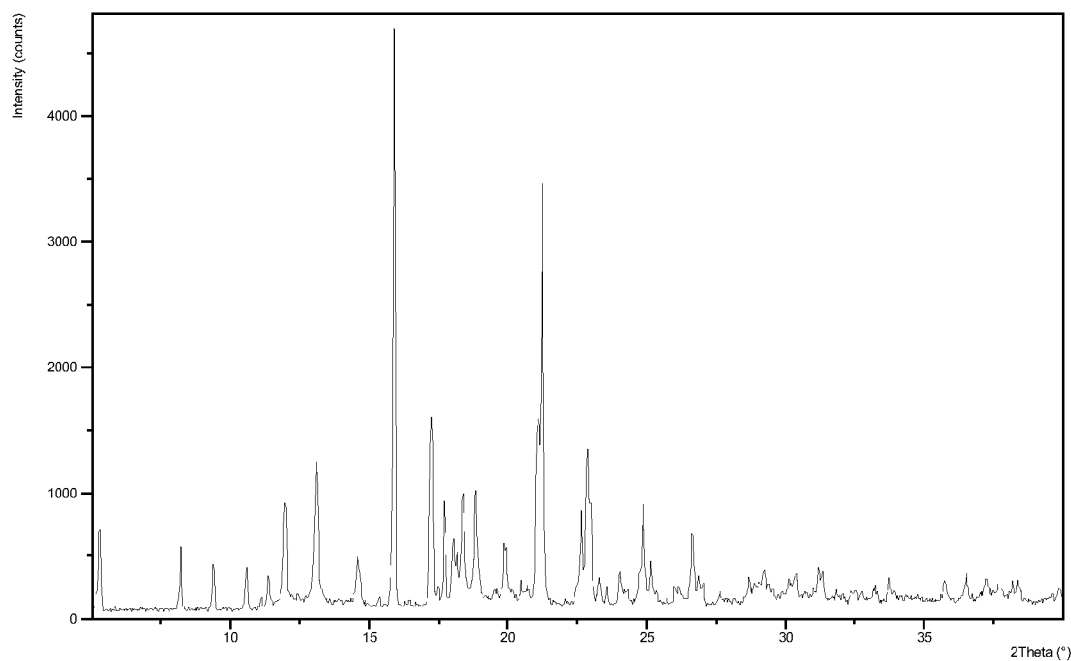
Figure 5:
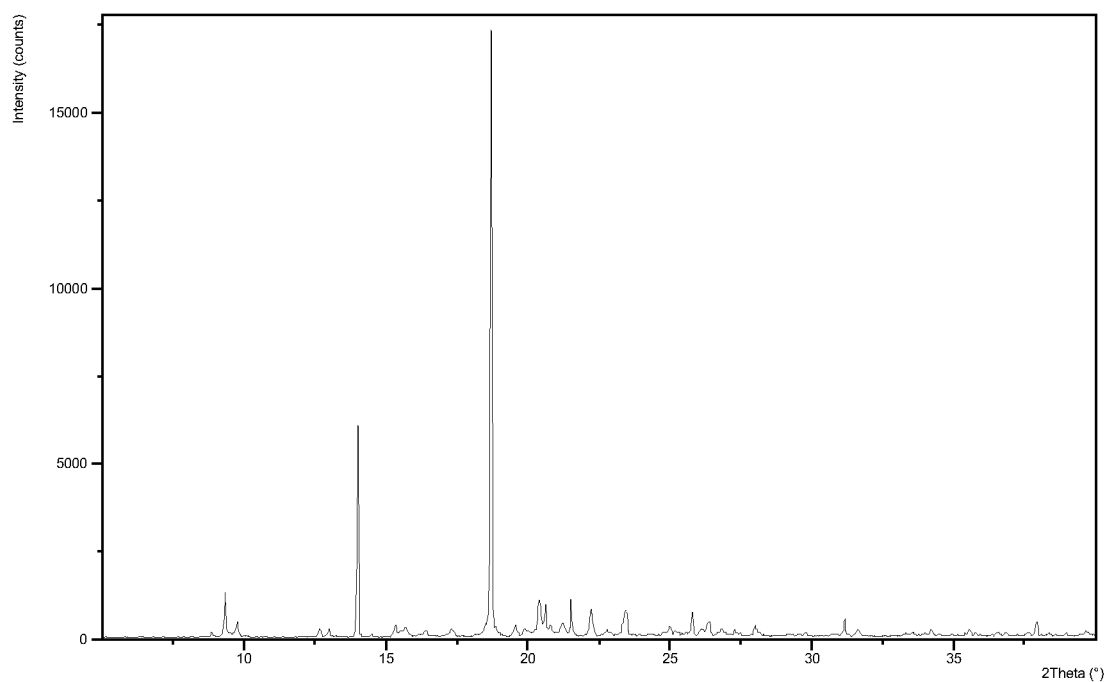

In one embodiment, the compound of the present invention is the DL-lactic acid addition salt (1:1) in a crystalline form, in particular in a purified form. In a further embodiment, said DL-lactic acid addition salt has peaks in a XRPD at approximately 5.30°, 8.81°, 9.44° and 17.24° 2θ, and in particular said DL lactic acid addition salt has an XRPD as depicted in FIG. 4.

Figure 17:
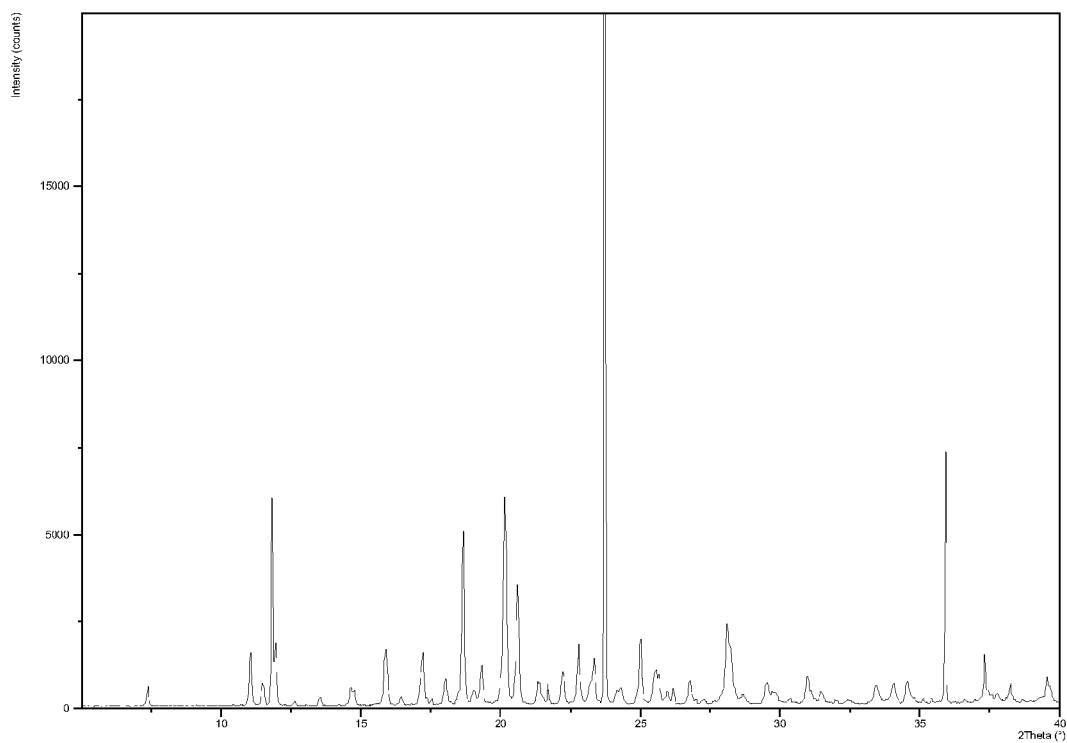
Figure 18:
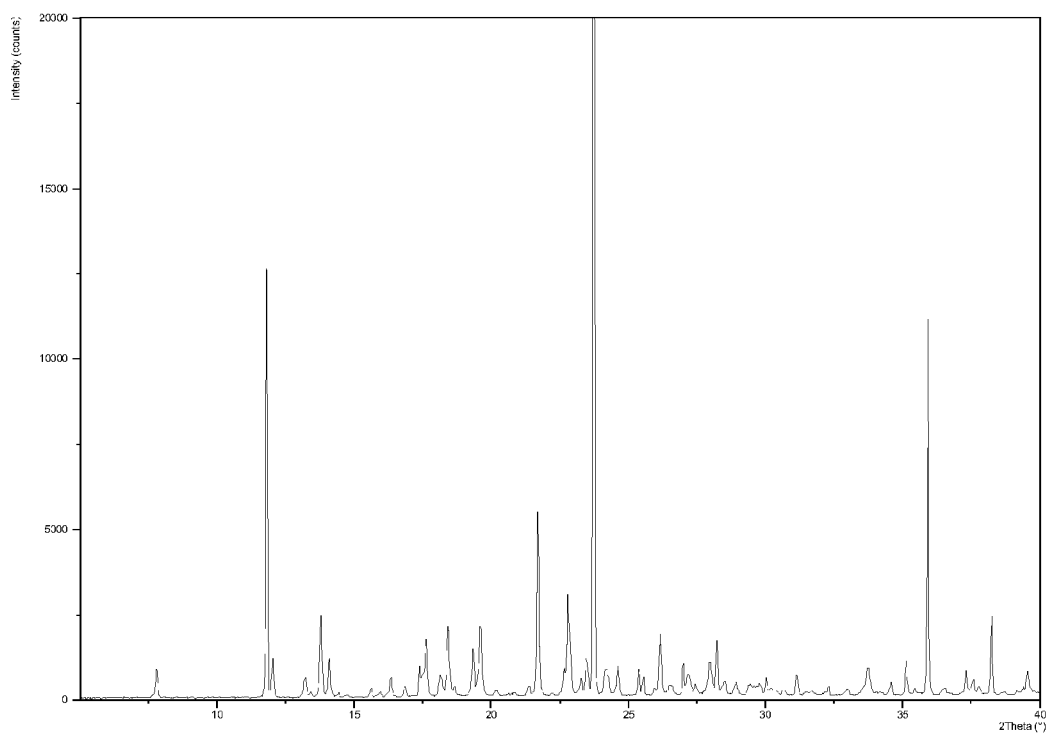

In one embodiment, the compound of the present invention is the L-aspartic acid addition salt (1:1) in a crystalline form, in particular in a purified form. In a further embodiment, said L-aspartic acid addition salt is unsolvated and has peaks in a XRPD at approximately 11.05°, 20.16°, 20.60°, 25.00° 2θ, and in particular said L-aspartic salt, when mixed with L-aspartic acid, has an XRPD as depicted in FIG. 17. In one embodiment, said L-aspartic acid addition salt is a hydrate, in particular in a purified form. In a further embodiment, said L-aspartic acid addition salt hydrate has peaks in a XRPD at approximately 7.80°, 13.80°, 14.10°, 19.63° 2θ, and in particular said L-aspartic addition salt hydrate, when mixed with L-aspartic acid, has an XRPD as depicted in FIG. 18.

Figure 19:
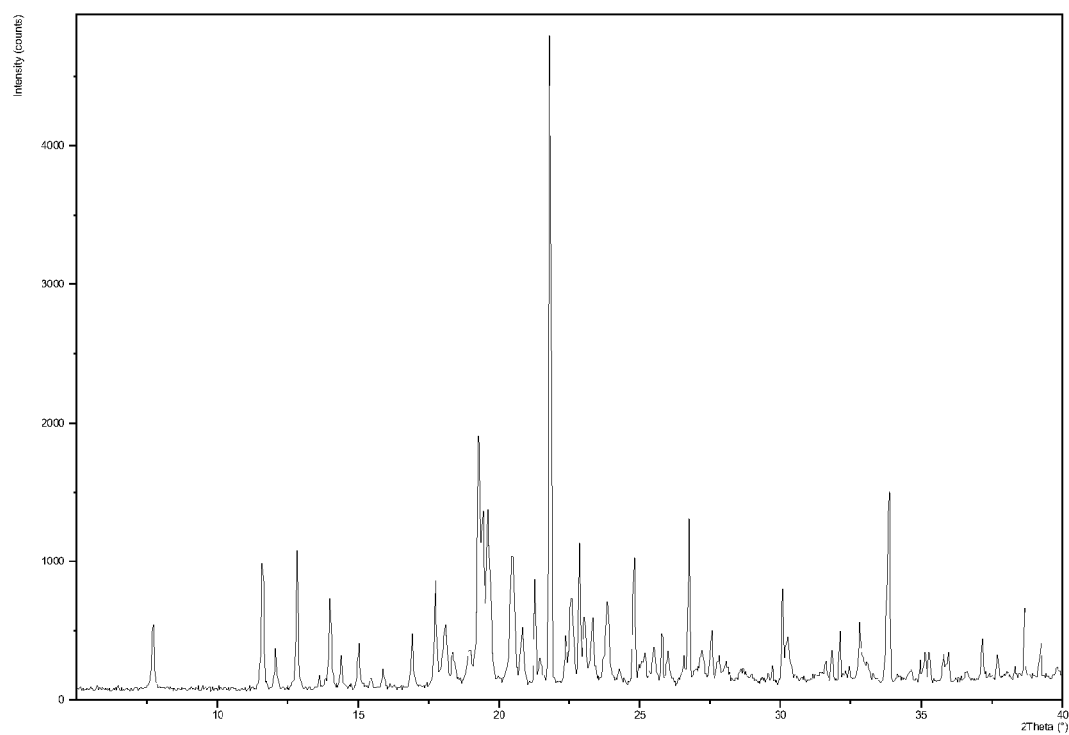

In one embodiment, the compound of the present invention is the glutamic acid addition salt (1:1) in a crystalline form, in particular in a purified form. In a further embodiment, said glutamic acid addition salt has peaks in a XRPD at approximately 7.71°, 14.01°, 19.26°, 22.57° 2θ, and in particular said glutamic acid salt, when mixed with glutamic acid monohydrate, has an XRPD as depicted in FIG. 19.

Figure 9:
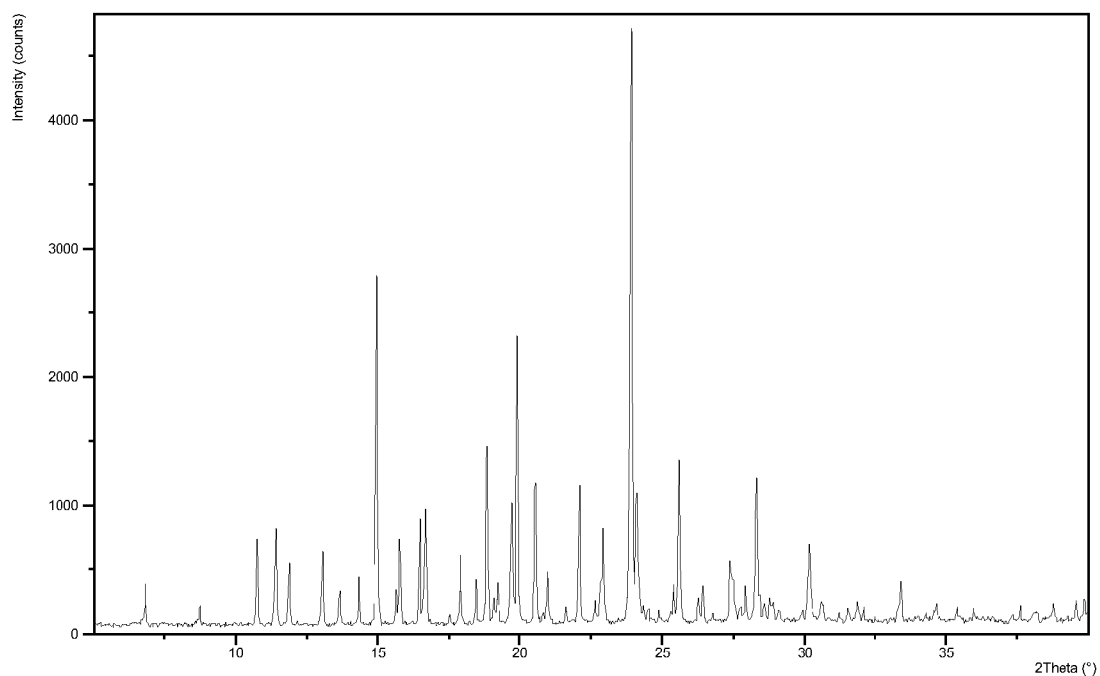
Figure 10:
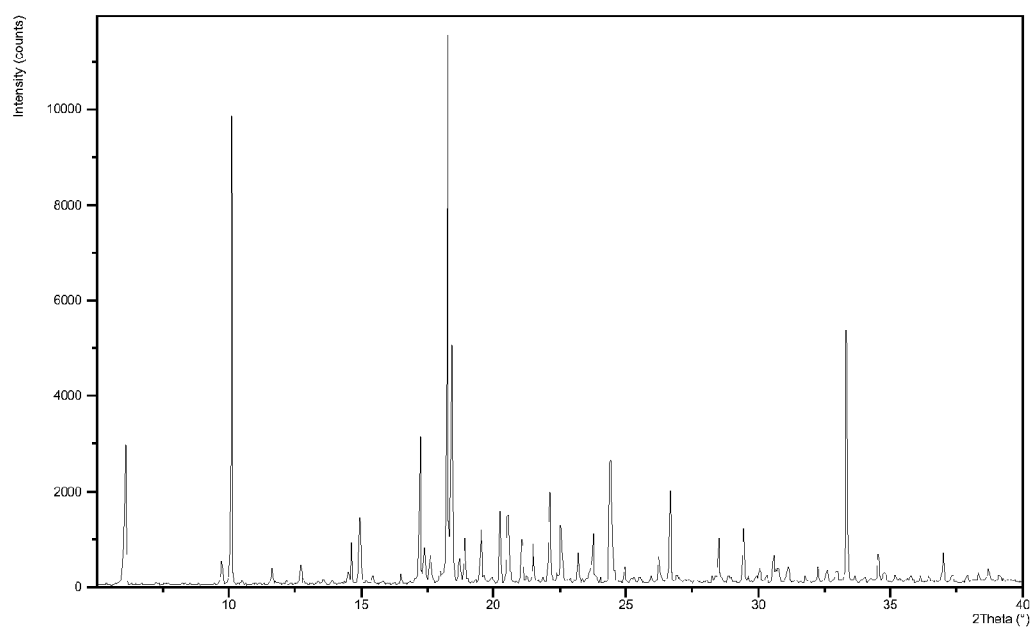

In one embodiment, the compound of the present invention is the malonic acid addition salt (1:1) in a crystalline form, in particular in a purified form. In a further embodiment, said malonic acid addition salt is the α-form and has peaks in a XRPD at approximately 10.77°, 16.70°, 19.93°, 24.01° 2θ, or said malonic acid addition salt is the β-form and has peaks in a XRPD at approximately 6.08°, 10.11°, 18.25°, 20.26° 2θ and in particular said malonic acid addition salt has an XRPD as depicted in FIG. 9 or 10.

Figure 8:
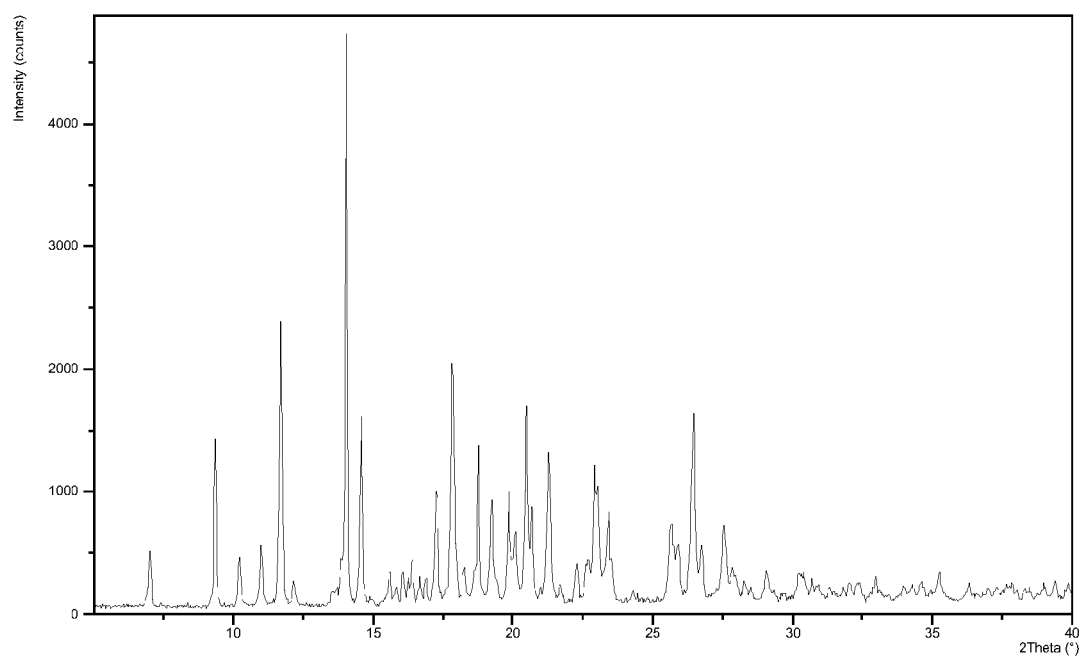

In one embodiment, the compound of the present invention is the glutaric acid addition salt (1:1) in a crystalline form, in particular in a purified form. In a further embodiment, said glutaric acid addition salt has peaks in a XRPD at approximately 9.39°, 11.70°, 14.05°, and 14.58° 2θ, and in particular said glutaric acid addition salt has an XRPD as depicted in FIG. 8.

As mentioned above, compounds of the present invention is particular well suited for the treatment of chronic pain. Chronic pain includes indications such as phantom limb pain, neuropathic pain, diabetic neuropathy, post-herpetic neuralgia (PHN), carpal tunnel syndrome (CTS), HIV neuropathy, complex regional pain syndrome (CPRS), trigeminal neuralgia/trigeminus neuralgia/tic douloureux, surgical intervention (e.g. post-operative analgesics), diabetic vasculopathy, capillary resistance or diabetic symptoms associated with insulitis, pain associated with angina, pain associated with menstruation, pain associated with cancer, dental pain, headache, migraine, tension-type headache, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain or geriatric pain.

In particular, the compounds of the present invention are useful for the treatment of mood disorders, such as depression associated with the above listed chronic pain indications.

Pain is defined by the International Association for the Study of Pain (IASP) as "an unpleasant sensory and emotional experience associated with actual or potential tissue damage, or described in terms of such damage (IASP Classification of chronic pain, $2^{nd}$ Edition, IASP Press (2002), 210). Even though pain is always subjective its causes or syndromes can be classified. "Neuropathic pain" as a subtype is defined by the IASP as "pain initiated or caused by a primary lesion or dysfunction in the nervous system".

Different subtypes of neuropathic pain are recognised by IASP, and examples are

Allodynia which is defined as "a pain due to a stimulus which does not normally provoke pain".

Causalgia which is defined as "a syndrome of sustained burning pain, allodynia and hyperpathia after a traumatic nerve lesion, often combined with vasomotor and sudomotor dysfunction and later trophic changes".

Hyperesthesia, which is defined as "increased sensitivity to stimulation, excluding the senses".

Neuralgia, which is defined as "Pain in the distribution of a nerve or nerves".

Neuritis, which is defined as "Inflammation of a nerve or nerves".

Neuropathy, which is defined as "a disturbance of function or pathological change in a nerve: in one nerve mononeuropathy, in several nerves mononeuropathy multiplex, if diffuse and bilateral, polyneuropathy". Neuropathy may be associated with e.g. diabetes in which case it is termed diabetic neuropathy.

Hyperalgesia, which is defined as "an increased response to a stimulus which is normally painful".

Hyperpathia, which is defined as "a painful syndrome characterized by an abnormally painful reaction to a stimulus, especially a repetitive stimulus, as well as an increased threshold".

The stimuli evoking the neuropathic pain may be mechanical or thermal.

The unique pharmacological profile of the compounds of the present inventions make them suitable for the treatment of other diseases, which are not directly related to chronic pain. 5-$HT_{2C}$ receptors are located e.g. on dopaminergic neurons where activation exerts a tonic inhibitory influence on the dopamine release, and 5-$HT_{2C}$ antagonists will effect an increase in the dopamine level. Data presented in example 2E show that compounds of the present invention do, in deed, bring about a dose dependent increase in the extra cellular dopamine levels in the brain. On this background it may be hypothesized that 5-$HT_{2C}$ antagonists are particular well-suited for the treatment of depression which is refractory to the treatment with selective serotonin reuptake inhibitors [*Psychopharmacol. Bull.*, 39, 147-166, 2006]. This hypothesis finds support in several clinical studies showing a combination of mirtazipine and SSRI to be superior to SSRI alone for the treatment of depressed patients with an inadequate clinical response (treatment resistant depression, TRD, or refractory depression) [*Psychother. Psychosom.*, 75, 139-153, 2006]. Mirtazapine is also a 5-$HT_2$ and a 5-$HT_3$ antagonist, which indicate that compounds exerting serotonin reuptake inhibition in combination with 5-$HT_2$ and 5-$HT_3$ antagonism, such as compounds of the present invention, are useful for the treatment of TRD, i.e. will increase the remission rate for patients suffering from treatment resistant depression.

Data presented in example 2F and 2G shows that the compounds of the present invention bring about an increase in the extracellular level of acetylcholine in the prefrontal cortex and ventral hippocampus. There is longstanding clinical evidence that increasing the acetylcholine levels in the brain is a way to treat Alzheimer's disease and cognitive impairment in general, cf. the use of acetylcholine esterase inhibitors in the treatment of Alzheimer's disease. On this background, compounds of the present invention are believed to be useful in the treatment of Alzheimer's disease and cognitive impairment, and also mood disorders, such as depression associated with Alzheimer's disease and cognitive impairment.

A segment of depressed patients will respond to treatment with e.g. SSRI in the sense that they will improve on clinically relevant depression scales, such as MADRD and HAMD, but where other symptoms, such as sleep disturbances and cognitive impairment remain. In the present context, these patients are referred to as partial responders. Due to the above discussed effects on the acetylcholine levels, the compounds of the present invention are expected to be useful in the treatment of the cognitive impairment in addition to the depression. Clinical studies have shown that the compound prazosin, which is an α-1 adrenergic receptor antagonist reduces sleep disturbances [*Biol. Psychiatry*, 61, 928-934, 2007]. Moreover, the 5-$HT_{2A}$ and 5-$HT_{2C}$ antagonism of the compounds of the present invention is also believed to have a sedative, sleep-improving effect [*Neuropharmacol*, 33, 467-471, 1994] wherefore the compounds of the present invention are useful for the treatment of partial responders, or rephrased that treatment of depressed patients with compounds of the present invention will reduce the fraction of partial responders.

Attention deficit hyperactivity disorder (ADHD) is one of the most common neurobehavioral disorders. ADHD is characterised by the presence of a triad of social and communicative impairments with restricted, repetitive or stereotyped behaviours. ADHD usually starts in childhood or adolescence, but symptoms may continue into adulthood. Atomoxetine is currently the only nonstimulant approved by FDA for the treatment of ADHD [*Drugs*, 64, 205-222, 2004]. Atomoxetine is a norepinephrine reuptake inhibitor, and this suggests that compounds of the present invention may be used in the treatment of ADHD. In addition, compounds of the present invention may have a sedative effect due to the α-1 adrenergic receptor and 5-$HT_2$ antagonism discussed above, which is beneficial in the treatment of ADHD.

Melancholia is a particular subtype of depression often connected to severe depression; this type of depression is also referred to as melancholic depression. Melancholia is associated with anxiety, dread of the future, insomnia, and loss of appetite. Compounds that inhibit both the serotonin and the norepinephrine reuptake, such as e.g. venlafaxine, have been shown to be particular effective in the treatment of patients with severe depression and melancholia [*Depres. Anxiety*, 12, 50-54, 2000]. As discussed above, compounds exerting 5-$HT_{2C}$ antagonism increase the dopamine level, wherefore such compounds would be expected to be effective in the treatment of melancholia [*Psychpharm. Bull.*, 39, 147-166, 2006]. Additionally, the α-1 adrenergic receptor and 5-$HT_2$ antagonism of the compounds of the present invention is expected to help normalise sleep, wherefore said compounds are useful in the treatment of melancholia.

FDA has recently approved sertraline and paroxetine, two SSRI's, for the treatment of post traumatic stress disorder (PTSD). Moreover, compounds having 5-$HT_{2A}$ antagonistic activity are useful as they are expected to be able to contain agitation, insomnia and explosiveness in PTSD patients [*Curr opinion Invest. Drug*, 4, 37-41, 2003]. Accordingly, the compounds of the present invention are expected to be useful in the treatment of PTSD.

Hot flushes is a symptom associated with the menopausal transition. Some women may suffer from this to an extent where it interferes with sleep or activities in general, and where treatment is necessary. Hormone replacement therapy with estrogen has been established practice for decades, however, recently concerns have been voiced on side effects, such as breast cancer and cardiac events. Clinical trials with SSRI and SNRI have shown that these compounds have an effect on hot flushes, albeit less than for estrogen [*J. Am. Med. Ass.*, 295, 2057-2071, 2006]. Treatment of hot flushes with compounds inhibiting serotonin and/or norepinephrine reuptake, e.g. compounds of the present invention could, however, be an alternative treatment for women who can not or will not accept estrogen.

Sleep apnea or obstructive sleep apnea-hyponea syndrome or obstructive sleep-disordered breathing is a disorder for which an effective pharmacotherapy remains to be identified. Several studies in animals, however, suggest that 5-$HT_3$ antagonists, e.g. compounds of the present invention may be effective in a therapeutic intervention [*Sleep*, 21, 131-136, 1998; *Sleep*, 8, 871, 878, 2001].

The 5-$HT_3$ antagonist odansetron has recently been shown effective in the treatment of craving and alcohol and drug abuse [*Drug Alc. Depend.*, 84, 256-263, 2006; *Pharmacol Therapeut.*, 111, 855-876, 2006]. This would seem to support the notion that 5-$HT_3$ antagonists, e.g. compounds of the present invention may be useful in the treatment of craving, such as alcohol, nicotine or carbohydrate craving; and alcohol and drug abuse.

Other suggested uses of 5-HT$_3$ antagonists include emesis, in particular chemo therapy-induced emesis, eating disorders, such as bulimia, and irritable bowel syndrome (IBS) [*Exp. Opin. Ther. Targets*, 11, 527-540, 2007].

The compounds of the present invention being endowed with a unique pharmacological profile are additionally expected to be useful in the treatment of affective disorders, depression, major depressive disorder, postnatal depression, depression associated with bipolar disorder, Alzheimer's disease, psychosis or Parkinson's disease, anxiety, general anxiety disorder, social anxiety disorder, obsessive compulsive disorder, panic disorder, panic attacks, phobia, social phobia, agoraphobia and stress urinary incontinence.

In one embodiment, the invention relates to a method of treating chronic pain, depression in partial responders, treatment resistant depression, Alzheimer's disease, cognitive impairment, ADHD, melancholia, PTSD, hot flushes, sleep apnea, alcohol, nicotine or carbohydrate craving, substance abuse, alcohol or drug abuse, emesis, eating disorders, IBS, affective disorders, depression, major depressive disorder, postnatal depression, depression associated with bipolar disorder, Alzheimer's disease, psychosis or Parkinson's disease, anxiety, general anxiety disorder, social anxiety disorder, obsessive compulsive disorder, panic disorder, panic attacks, phobia, social phobia, agoraphobia or stress urinary incontinence, the method comprising administering to a patient in need thereof a therapeutically effective amount of compound I. In one embodiment, said patient being treated for any of the above listed diseases has initially been diagnosed with said disease.

In one embodiment, the invention relates to a method for the treatment of chronic pain, the method comprising administering to a patient in need thereof a therapeutically effective amount of compound I. In one embodiment, said chronic pain is selected from phantom limb pain, neuropathic pain, diabetic neuropathy, post-herpetic neuralgia (PHN), carpal tunnel syndrome (CTS), HIV neuropathy, complex regional pain syndrome (CPRS), trigeminal neuralgia/trigeminus neuralgia/tic douloureux, surgical intervention (e.g. post-operative analgesics), diabetic vasculopathy, capillary resistance or diabetic symptoms associated with insulitis, pain associated with angina, pain associated with menstruation, pain associated with cancer, dental pain, headache, migraine, tension-type headache, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain or geriatric pain.

In one embodiment, said chronic pain is neuropathic pain.

In one embodiment, said neuropathic pain is selected from hyperpathia, hyperalgesia, neuropathy, diabetic neuropathy, neuritis, neuralgia, hyperesthesia, causalgia, and allodynia.

In an embodiment, the compound of the invention is administered in an amount of about 0.001 to about 100 mg/kg body weight per day.

A typical oral dosage is in the range of from about 0.001 to about 100 mg/kg body weight per day, preferably from about 0.01 to about 50 mg/kg body weight per day, administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

A typical oral dosage for adults is in the range of 1-100 mg/day of a compound of the present invention, such as 1-30 mg/day, or 5-25 mg/day. This may typically be achieved by the administration of 0.1-50 mg, such as 1-25 mg, such as 1, 5, 10, 15, 20 or 25 mg of the compound of the present invention once or twice daily.

A "therapeutically effective amount" of a compound as used herein means an amount sufficient to cure, alleviate or partially arrest the clinical manifestations of a given disease and its complications in a therapeutic intervention comprising the administration of said compound. An amount adequate to accomplish this is defined as "therapeutically effective amount". The term also includes amounts sufficient to cure, alleviate or partially arrest the clinical manifestations of a given disease and its complications in a treatment comprising the administration of said compound. Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatment are two separate aspect of the invention. The patient to be treated is preferably a mammal, in particular a human being.

In one embodiment, the invention relates to the use of the present invention in the manufacture of a medicament for the treatment of chronic pain, depression in partial responders, treatment resistant depression, Alzheimer's disease, cognitive impairment, ADHD, melancholia, PTSD, hot flushes, sleep apnea, alcohol, nicotine or carbohydrate craving, substance abuse, alcohol or drug abuse, emesis, eating disorders, IBS, affective disorders, depression, major depressive disorder, postnatal depression, depression associated with bipolar disorder, Alzheimer's disease, psychosis or Parkinson's disease, anxiety, general anxiety disorder, social anxiety disorder, obsessive compulsive disorder, panic disorder, panic attacks, phobia, social phobia, agoraphobia or stress urinary incontinence.

In one embodiment, the invention relates to the use of the present invention in the manufacture of a medicament for the treatment of chronic pain, such as neuropathic pain.

In one embodiment, the invention relates to of the present invention for use as a medicament for the treatment of chronic pain, depression in partial responders, treatment resistant depression, Alzheimer's disease, cognitive impairment, ADHD, melancholia, PTSD, hot flushes, sleep apnea, alcohol, nicotine or carbohydrate craving, substance abuse, alcohol or drug abuse, emesis, eating disorders, IBS, affective disorders, depression, major depressive disorder, postnatal depression, depression associated with bipolar disorder, Alzheimer's disease, psychosis or Parkinson's disease, anxiety, general anxiety disorder, social anxiety disorder, obsessive compulsive disorder, panic disorder, panic attacks, phobia, social phobia, agoraphobia or stress urinary incontinence.

In one embodiment, the invention relates to compounds of the present for use as a medicament for the treatment of chronic pain, such as neuropathic pain The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 50 mg, such as 1 mg, 5 mg 10 mg, 15 mg, 20 mg or 25 mg of a compound of the present invention.

For parenteral routes such as intravenous, intrathecal, intramuscular and similar administration, typically doses are in the order of about half the dose employed for oral administration.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Capsules comprising a compound of the present invention may be prepared by mixing a powder comprising said compound with microcrystalline cellulose and magnesium stearate and place said powder in a hard gelatine capsule. Optionally, said capsule may be coloured by means of a suitable pigment. Typically, capsules will comprise 0.25-20% of a compound of the present invention, such as 0.5-1.0%, 3.0-4.0%, 14.0-16.0% of a compound of the present invention. These strengths can be used to conveniently deliver 1, 5, 10, 15, 20 and 25 mg of a compound of the present invention in a unit dosage form.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Compound I may be prepared as outlined in WO 2003/029232. Salts of compound I may by addition of an appropriate acid followed by precipitation. Precipitation may be brought about by e.g. cooling, removal of solvent, addition of another solvent or a mixture thereof.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Analytical Methods

X-Ray powder diffractograms (XRPD) were measured on a PANalytical X'Pert PRO X-Ray Diffractometer using $CuK_{\alpha 1}$ radiation. The samples were measured in reflection mode in the 2θ-range 5-40° using an X'celerator detector. Elemental composition (CHN) was measured on an Elementar Vario EL instrument from Elementar. About 4 mg of sample was used for each measurement, and the results are given as mean values of two measurements.

Example 1a

HBr Salt of Compound I

To 442 grams of stirred and slightly heated (approx. 45° C.) 4-(2-p-Tolylsulfanyl-phenyl)-piperidine-1-carboxylic acid ethyl ester as an oil was added 545 ml of 33 wt-% HBr in AcOH (5.7 M, 2.5 eqv.). This mixing gives a 10° C. exotherm. After final addition the reaction mixture is heated to 80° C. and left for 18 hours. A sample is withdrawn and analysed by HPLC and if not completed more 33 wt-% HBr in AcOH must be added. Otherwise the mixture is cooled to 25° C. making the product 4-(2-p-Tolylsulfanyl-phenyl)-piperidine hydrobromide to precipitate. After one hour at 25° C. the thick suspension is added 800 ml diethylether. Stirring is continued for another hour before the product is isolated by filtration, washed with 400 ml diethylether and dried in vacuum at 40° C. overnight. The hydrobromide of compound I was isolated as white solid.

Example 1b

HBr Salt of Compound I 2-(4-tolylsulfanyl)-phenyl bromide

In a stirred nitrogen covered reactor N-methyl-pyrrolidone, NMP (4.5 L) was flushed with nitrogen for 20 minutes. 4-Methylbenzenethiol (900 g, 7.25 mol) was added and then 1,2-dibromobenzene (1709 g, 7.25 mol). Potassium tert-butoxide (813 g, 7.25 mol) was finally added as the last reactant. The reaction was exothermic giving a temperature rise of the reaction mixture to 70° C. The reaction mixture was then heated to 120° C. for 2-3 hours. The reaction mixture was cooled to room temperature. Ethyl acetate (4 L) was added and aqueous sodium chloride solution (15%, 2.5 L). The mixture was stirred for 20 minutes. The aqueous phase was separated and extracted with another portion of ethyl acetate (2 L). The aqueous phase was separated and the organic phases were combined and washed with sodium chloride solution (15%, 2.5 L) The organic phase was separated, dried with sodium sulphate and evaporated at reduced pressure to a red oil which contains 20-30% NMP. The oil was diluted to twice the volume with methanol and the mixture was refluxed. More methanol was added until a clear red solution was obtained. The solution was cooled slowly to room temperature while seeded. The product crystallises as off white crystals, they were isolated by filtration and washed with methanol and dried at 40° C. in a vacuum oven until constant weight.

Ethyl 4-hydroxy-4-(2-(4-tolylsulfanyl)phenyl)-piperidin-1-carboxylate

In a stirred reactor under nitrogen cover 2-(4-tolylsulfanyl)-phenyl bromide (600 g, 2.15 mol) was suspended in heptane (4.5 L). At room temperature 10M BuLi in hexane (235 mL, 2.36 mol) was added over 10 minutes. Only a small exotherm was noticed. The suspension was stirred for 1 hour at ambient temperature and then cooled down to −40° C. 1-Carbethoxy-4-piperidone (368 g, 2.15 mol) dissolved in THF (1.5 L) was added at a rate not faster than the reaction temperature was kept below −40° C. When the reaction has gone to completion, it was warmed to 0° C. and 1M HCl (1 L) was added keeping the temperature below 10° C. The acid aqueous phase was separated and extracted with ethyl acetate (1 L). The organic phases were combined and extracted with sodium chloride solution (15%, 1 L). The organic phase was dried over sodium sulphate and evaporated to a semi crystalline mass. It was slurried with ethyl ether (250 mL) and filtered off. Dried in an vacuum oven at 40° C. until constant weight.

Ethyl 4-(2-(4-tolylsulfanyl)phenyl)-piperidin-1-carboxylate

Trifluoroacetic acid (2.8 kg, 24.9 mol) and triethylsilane (362 g, 3.1 mol) was charged in a reactor with an efficient stirrer. Ethyl 4-hydroxy-4-(2-(4-tolylsulfanyl)phenyl)-piperidin-1-carboxylate (462 g, 1.24 mol) was added via a powder funnel in portions. The reaction was slightly exothermic. The temperature rose to 50° C. After the addition was finalised the reaction mixture was warmed to 60° C. for 18 hours. The reaction mixture was cooled down to room temperature. Toluene (750 mL) and water (750 mL) was added. The organic phase was isolated and the aqueous phase was extracted with another portion of toluene (750 mL). The organic phases were combined and washed with sodium chloride solution (15%, 500 mL) and dried over sodium sulphate. The sodium sulphate was filtered off, the filtrate evaporated at reduced pressure to a red oil which was processed further in the next step.

4-(2-(4-tolylsulfanyl)phenyl)-piperidin hydrobromide

The crude ethyl 4-(2-(4-tolylsulfanyl)phenyl)-piperidin-1-carboxylate as a red oil from example 3 was mixed in a stirred reactor with hydrobromic acid in acetic acid (40%, 545 mL, 3.11 mol). The mixture was heated at 80° C. for 18 hours. The reaction mixture was cooled down to room temperature. During the cooling the product crystallises out. After 1 hour at room temperature ethyl ether (800 mL) was added to the reaction mixture, and the mixture was stirred for another hour. The product was filtered off, washed with ethyl ether and dried in a vacuum oven at 50° C. until constant weight.

Example 1c

Recrystallisation of the HBr Salt of Compound I

A mixture of 10.0 grams of the HBr salt of compound I, e.g. prepared as above, was heated to reflux in 100 ml $H_2O$. The mixture became clear and fully dissolved at 80-90° C. To the clear solution was added 1 gram of charcoal and reflux was continued for 15 minutes before filtered and left to cool spontaneously to room temperature. During the cooling precipitation of white solid took place and the suspension was stirred for 1 hour at room temperature. Filtration and drying in vacuum at 40° C. overnight produced 6.9 grams (69%) of the HBr acid addition salt of compound I. See FIG. 1 for XRPD. Elemental analysis: 3.92% N, 59.36% C, 6.16% H (theory: 3.85% N, 59.34% C, 6.09% H)

Example 1d

Preparation of Stock-Solutions of Free Base

A mixture of 500 ml ethyl acetate and 200 ml $H_2O$ was added 50 grams of the HBr salt of compound I producing a two-phased slurry. To this slurry was added approximately 25 ml conc. NaOH that caused formation of a clear two-phased solution (pH was measured to 13-14). The solution was stirred vigorously for 15 minutes and the organic phase was separated. The organic phase was washed with 200 ml $H_2O$, dried over $Na_2SO_4$, filtered and evaporated in vacuum at 60° C. producing the free base in 38 grams yield (99%) as an almost colourless oil.

Dissolving 10 grams of the oil and adjusting the volume to 150 ml using ethyl acetate produced a 0.235 M stock-solution in ethyl acetate from which aliquots of 1.5 ml (100 mg of the free base) was used.

Dissolving 10 grams of the oil and adjusting the volume to 100 ml using 96-vol % EtOH produced a 0.353 M stock-solution in EtOH from which aliquots of 1.0 ml (100 mg of the free base) was used.

Example 1e

Formation of Salts Using Stock-Solutions of the Free Base

The given aliquots were placed in test tubes and while stirred the appropriate amount of acid was added as indicated in Table 1. If the acid was a liquid it was added neat otherwise it was dissolved in the given solvent prior to addition. After mixing and precipitation stirring was continued overnight and the precipitate collected by filtration. Before drying in vacuum at 30° C. a small reference sample was withdrawn and dried at room temperature without vacuum. This procedure was included in order to test for solvates. Some results are presented in Table 1. XRPD diffractograms are shown in FIGS. 1-22, and selected peak positions are tabulated in Table 2. Table 3 shows the solubilities of compounds of the present invention in water together with pH in the resulting saturated solution. The column "Precipitate" shows whether the precipitate isolated after the solubility determination is identical to the compound dissolved, which is indicative of the formation of hydrates.

TABLE 1

| Acid (Base:Acid) | MW (g/mol) | Amount of Acid (mg or μl) | Solvent | CHN (exp.) | | | CHN (theory) | | |
|---|---|---|---|---|---|---|---|---|---|
| Palmitic acid, hexadecanoic acid 1:1 | 256.42 | 90.5 | EtOAc | 75.36 | 9.77 | 2.46 | 75.64 | 9.9 | 2.6 |
| DL-Lactic acid, DL-2-hydroxypropionic acid 1:1 | 90.1 | 31.8 | EtOAc | 66.88 | 7.26 | 3.52 | 67.53 | 7.29 | 3.75 |
| Adipicacid, 1,6-hexanedioic acid 1:1 | 146.14 | 51.6 | EtOAc | 66.08 | 7.23 | 2.98 | 67.1 | 7.27 | 3.26 |
| Adipicacid, 1,6-hexanedioic acid 2:1 | 146.14 | 25.8 | EtOAc | 70.66 | 7.32 | 3.82 | 70.75 | 7.35 | 3.93 |
| Fumaric acid 1:1 | 116.01 | 40.9 | EtOH | 65.71 | 6.41 | 3.35 | 66.14 | 6.31 | 3.51 |
| Glutaric acid, 1,5-pentanedioic acid 1:1 | 132.12 | 46.6 | EtOAc | 66.09 | 6.97 | 3.2 | 66.48 | 7.03 | 3.37 |
| Malonic acid 1:1 | 104.1 | 36.7 | EtOAc | 65.04 | 6.53 | 3.54 | 65.09 | 6.5 | 3.62 |
| Oxalic acid 1:1 | 90.1 | 31.8 | EtOH | 64.28 | 6.41 | 3.61 | 64.32 | 6.21 | 3.75 |
| Sebacoinic acid, 1,8-octanedioic acid 2:1 | 202.02 | 35.6 | EtOAc | 71.79 | 7.86 | 3.58 | 71.83 | 7.86 | 3.64 |
| Succinic acid, 1,4-butanedioic acid, 2:1 | 118.1 | 20.8 | EtOAc | 65.65 | 6.86 | 3.4 | 65.80 | 6.78 | 3.49 |
| | | | | | | | (1:1 salt formed) | | |
| L-malic acid, L-2-hydroxy butanedioic acid 1:1, α | 134.1 | 47.3 | EtOAc | 62.87 | 6.20 | 3.22 | 63.29 | 6.52 | 3.36 |
| L-malic acid, L-2-hydroxy butanedioic acid 1:1, β | 134.1 | 47.3 | EtOH | 62.99 | 6.66 | 3.13 | 63.29 | 6.52 | 3.36 |
| D-tartaric acid, D-2,3-dihydroxy butanedioic acid 1:1 | 150.1 | 53.0 | EtOH | 60.67 | 6.4 | 3.07 | 60.95 | 6.28 | 3.23 |
| L-aspartic acid 1:1 | 133.1 | 47.0 | EtOH | 59.31 | 6.7 | 7.1 | 63.43 | 6.78 | 6.73 |
| | | | | (contains excess of acid) | | | | | |
| Glutamic acid 1:1 | 165.15 | 58.3 | EtOH | 56.38 | 6.88 | 7.35 | 56.46 | 6.94 | 7.06 |
| | | | | (contains excess of acid) | | | (for 1:1-salt and acid-monohydrate 1:1) | | |

TABLE 1-continued

| Acid (Base:Acid) | MW (g/mol) | Amount of Acid (mg or μl) | Solvent | CHN (exp.) | | | CHN (theory) | | |
|---|---|---|---|---|---|---|---|---|---|
| Citric acid 2:1 | 192.13 | 33.9 | EtOAc | 65.93 | 6.72 | 3.44 | 66.46 | 6.64 | 3.69 |
| HCl/Et$_2$O 1:1 | 2 M | 176.4 | EtOH | | | | | | |
| Phosphoric acid 1:1 | 14.7 M | 24.0 | EtOAc | 55.79 | 6.47 | 3.43 | 56.68 | 6.34 | 3.67 |

TABLE 2

Selected X-ray peak positions (°2θ), 2:1 means
2 bases to 1 acid. All values +−0.1°

| Palmitate | 7.00 | 16.34 | 22.73 | 28.21 |
|---|---|---|---|---|
| Stearate | 6.70 | 15.52 | 21.81 | 28.91 |
| Lactate | 5.30 | 8.18 | 9.44 | 17.24 |
| Lactate hydrate | 11.67 | 16.70 | 18.25 | 21.76 |
| hydroxyl-isobutyrate | 5.09 | 16.60 | 20.38 | 27.37 |
| Sebacoin acid salt | 7.18 | 12.53 | 21.11 | 24.19 |
| Adipinic acid salt 2:1 | 8.03 | 13.52 | 17.90 | 24.60 |
| Adipinic acid salt 1:1 α | 9.33 | 14.01 | 18.72 | 20.63 |
| Adipinic acid salt 1:1 β | 15.69 | 21.53 | 25.81 | 31.18 |
| Glutarate 1:1 | 9.39 | 11.70 | 14.05 | 14.58 |
| Succinate 1:1 | 11.74 | 14.33 | 17.75 | 26.84 |
| Fumarate 1:1 | 8.90 | 11.47 | 19.25 | 22.33 |
| Fumarate 2:1 | 8.49 | 12.48 | 17.78 | 23.97 |
| Maleate 1:1 | 12.11 | 15.51 | 17.48 | 22.53 |
| Maleate 1:1 hydrate | 12.81 | 18.76 | 20.53 | 27.31 |
| Malonate α | 10.77 | 16.70 | 19.93 | 24.01 |
| Malonate β | 6.08 | 10.11 | 18.25 | 20.26 |
| Aspartate | 11.05 | 20.1 | 20.60 | 25.00 |
| Aspartate hydrate | 7.80 | 13.80 | 14.10 | 19.63 |
| Glutamate | 7.71 | 14.01 | 19.26 | 22.57 |
| Oxalate | 14.68 | 17.45 | 19.50 | 23.90 |
| Malate 1:1 α | 8.30 | 12.04 | 17.23 | 20.67 |
| Malate 1:1 β | 10.91 | 12.87 | 14.14 | 26.16 |
| Malate hydrate | 12.30 | 15.56 | 19.56 | 23.30 |
| D-tartrate (from EtOH) | 5.08 | 17.18 | 19.42 | 22.10 |
| Hydrochloride | 12.44 | 16.72 | 19.45 | 25.02 |
| Hydrobromide | 6.08 | 14.81 | 19.26 | 25.38 |
| Hydrobromide 1-PrOH solvate | 6.57 | 13.12 | 19.07 | 24.77 |

TABLE 3

| Acid (Base:Acid) | Solubility (mg/ml) | Resulting pH | Precipitate |
|---|---|---|---|
| Palmitic acid, hexadecanoic acid 1:1 | 0.4 | 8.6 | =start |
| DL-Lactic acid, DL-2-hydroxypropionic acid 1:1 | >150 | 6.1 | =start (after evaporation) |
| Adipicacid, 1,6-hexanedioic acid 1:1 | 2.5 | 4.0 | Partly 2:1 salt |
| Adipicacid, 1,6-hexanedioic acid 2:1 | 1.0 | 7.8 | =start |
| Fumaric acid 1:1 | 0.2 | 3.3 | =start |
| Glutaric acid, 1,5-pentanedioic acid 1:1 | 13 | 4.6 | =start |
| Malonic acid 1:1 (α) | 5.2 | 4.0 | =new form (β) |
| Oxalic acid 1:1 | 1.1 | 2.7 | =Start |
| Sebacoinic acid, 1,8-octanedioic acid 2:1 | 0.7 | 5.5 | =Start |
| Succinic acid, 1,4-butanedioic acid, 2:1 | 2.0 | 4.0 | Hydrate |
| L-malic acid, L-2-hydroxy butanedioic acid 1:1, β | 2.8 | 4.0 | Hydrate |
| D-tartaric acid, D-2,3-dihydroxy butanedioic acid 1:1 | 1.8 | 3.5 | Hydrate |
| L-aspartic acid 1:1 | 39 | 4.3 | Hydrate |
| Glutamic acid 1:1 | >35 | 4.6 | — |
| Citric acid 2:1 | 0.5 | 4.7 | =Start |
| Phosphoric acid 1:1 | 6.0 | 2.0 | ? |
| HCl | 4.5 | 6.8 | =Start |
| HBr | 2.4 | 7.0 | =Start |

Example 2A

Serotonin (5-HT) and Norepinephrine (NE) Reuptake Inhibition

Aliquots of test compound and rat cortical synaptosome preparation were pre-incubated for 10 min/37° C., and then added [$^3$H]NE or [$^3$H]5-HT (final concentration 10 nM). Non-specific uptake was determined in the presence of 10 μM talsupram or citalopram and the total uptake was determined in the presence of buffer. Aliquots were incubated for 15 minutes at 37° C. After the incubation [$^3$H]NE or [$^3$H]5-HT taken up by synaptosomes was separated by filtration through Unifilter GF/C, presoaked in 0.1% PEI for 30 minutes, using a Tomtec Cell Harvester program. Filters were washed and counted in a Wallac MicroBeta counter.

At NET compounds of the present invention display an $IC_{50}$ value of 23 nM. At SERT compounds of the present invention display an $IC_{50}$ value of 8 mM.

Example 2B

5-HT$_{2A}$ Antagonism

Compounds of the present invention were tested for affinities towards serotonin receptors and was found to exhibit an antagonistic profile with affinity at 5-HT$_{2A}$ receptors ($K_i$ 54 mM). The affinity is calculated from $Y=100/(1+10^{(X-logIC_{50})})$ where Y denotes % binding and X denotes the concentration of compound. 5 concentrations of compound (1, 10, 30, 100, 1000 nM) were used to calculate the $IC_{50}$ value. Ki was calculated from the Cheng Prusoff equation $Ki=(IC_{50}/(1+([L]/Kd))$ Affitiny was determined at MDL Pharmaservices catalogue number 271650.

In mammalian cells expressing human 5-HT$_{2A}$ receptors compounds of the present invention display competitive antagonistic properties. The compounds bind to 5-HT$_{2A}$ receptors with a Ki of <100 nM and in a functional assay the compounds antagonise 5-HT evoked release of $Ca^{2+}$ from intracellular stores with a Kb of 67 nM. A schild analysis revealed competitive antagonism with a Kb of 100 nM.

The experiment was carried out as follows. 2 or 3 days before the experiment CHO cells expressing 250 fmol mg human 5-HT$_{2A}$ receptors are plated at a density sufficient to yield a mono-confluent layer on the day of the experiment. The cells are dye loaded ($Ca^{2+}$-kit from Molecular Devices) for 60 minutes at 37° C. in a 5% $CO_2$ incubator at 95% humidity. Basal fluorescence was monitored in a fluorometric imaging plate reader or FLIPR$^{384}$ from Molecular Devices (Sunnyvale, Calif.) with an excitation wavelength of 488 nm and an emission range of 500 to 560 nm. Lacer intensity was set to a suitable level to obtain basal values of approximately 8000-10000 fluorescence units. The variation in basal fluorescence should be less than 10%. $EC_{50}$ values are assessed using increasing concentrations of test compound covering at least 3 decades. pA2 values are assessed challenging full dose response curves of 5-HT with four different concentrations of compound (150, 400 1500 and 4000 nM). Kb values were also assessed challenging 2 decades of concentrations of test substances with $EC_{85}$ of 5-HT. Test substances are added to the cells 5 minutes before the 5-HT. $K_i$ values are calculated using Cheng-Prusoff equation.

Example 2C

5-HT$_{3A}$ Receptor Antagonism

In oocytes expressing human-homomeric 5-HT$_{3A}$ receptors 5-HT activates currents with an $EC_{50}$ of 2600 nM. This current can be antagonised with classical 5-HT$_3$ antagonists such as ondansetron. Ondansetron displays a Ki value below 1 nM in this system. Compounds of the present invention exhibit potent antagonism in low concentrations (0.1 nM-100 nM) ($IC_{50}$~10 nM/Kb~2 mM) and agonistic properties when applied in higher concentrations (100-100000 nM) ($EC_{50}$~2600 nM) reaching a maximal current of approximately 70-80% of the maximal current elicited by 5-HT itself. In oocytes expressing rat-homomeric 5-HT$_{3A}$ receptors 5-HT activates currents with an $EC_{50}$ of 3.3 μM. The experiments were carried out as follows. Oocytes were surgically removed from mature female *Xenepus laevis* anaesthetized in 0.4% MS-222 for 10-15 min. The oocytes were then digested at room temperature for 2-3 hours with 0.5 mg/ml collagenase (type IA Sigma-Aldrich) in OR2 buffer (82.5 mN NaCl, 2.0 mM KCl, 1.0 mM MgCl2 and 5.0 mM HEPES, pH 7.6). Oocytes avoid of the follicle layer were selected and incubated for 24 hours in Modified Barth's Saline buffer [88 mM NaCl, 1 mM KCl, 15 mM HEPES, 2.4 mM NaHCO$_3$, 0.41 mM CaCl$_2$, 0.82 mM MgSO$_4$, 0.3 mM Ca(NO$_3$)$_2$] supplemented with 2 mM sodium pyruvate, 0.1 U/l penicillin and 0.1 μg/l streptomycin. Stage 1V-1V oocytes were identified and injected with 12-48 nl of nuclease free water containing 14-50 pg of cRNA coding for human 5-HT3A receptors and incubated at 18° C. until they were used for electrophysiological recordings (1-7 days after injection). Oocytes with expression of human 5-HT3 receptors were placed in a 1 ml bath and perfused with Ringer buffer (115 mM NaCl, 2.5 mM KCl, 10 mM HEPES, 1.8 mM CaCl$_2$, 0.1 mM MgCl$_2$, pH 7.5). Cells were impaled with agar plugged 0.5-1 MΩ electrodes containing 3 M KCl and voltage clamped at −90 mV by a GeneClamp 500 B amplifier. The oocytes were continuously perfused with Ringer buffer and the drugs were applied in the perfusate. 5-HT agonist-solutions were applied for 10-30 sec. The potencies of 5-HT$_3$ receptor antagonists were examined by measuring concentration-response against 10 μM 5-HT stimulation.

Example 2D

α$_{1A}$ Receptor Antagonism

Compounds of the present invention were tested for affinities towards the α$_{1A}$ receptor and was found to exhibit an antagonistic profile with medium affinity for α$_{1A}$ receptors (Ki=34 nM).

On the day of the experiments membranes (see below for description of membrane preparation) are thawed and homogenized in buffer using an ultra turrax and diluted to the desired concentration (5 μg/well~5 μg/900 μl, store on ice until use).

The experiment is initiated by mixing of 50 μl test compound, 50 μl [$^3$H]-Prazosin and 900 μl membranes, and the mixture is incubated for 20 minutes at 25° C. Non-specific binding is determined in the presence of 10 μM WB-4101 and the total binding is determined in the presence of buffer. After the incubation, bound ligand is separated from unbound by filtration through Unifilter GF/B, presoaked in 0.1% PEI for 30 minutes, using a Tomtec Cell Harvester program (D4.2.4). 96 well. Filters are washed 3 times with 1 ml ice-cold buffer, dried at 50° C. and 35 μl scintillation liquid/well is added to the filters. Bound radioactivity is counted in a Wallac OY 1450 MicroBeta. The affinity is calculated from $Y=100/(1+10^{(X-logIC_{50})})$ where Y denotes % binding and X denotes the concentration of compound. Concentrations of compound covering 2 decades were used to calculate the $IC_{50}$ value. Ki was calculated from the Cheng Prusoff equation $Ki=(IC_{50}/(1+([L]/Kd))$ In a functional assay compounds of the present invention antagonises adrenaline evoked release of Ca$^{2+}$ from intracellular stores and a functional assay revealed that compounds were antagonists.

These experiments were carried out essentially as described below.

All cells were cultured in DMEM medium supplemented with 10% BCS, 4 mM L-glutamine (or 2 mM in the case of COS-7), and 100 units/ml penicillin plus 100 μg/ml streptomycin, at 37° C., in 5% CO2.

Twenty-four hours prior to assays, CHO cells expressing the human alpha$_{1A-7}$ receptors were seeded into 384-well black wall microliter plates coated with poly-D-lysine. Culture medium was aspirated and cells were dye-loaded with 1.5 μM Fluo-4 in assay buffer composed of Hank's Balanced Salt Solution (138 mM NaCl, 5 mM KCl, 1.3 mM CaCl$_2$, 0.5 mM MgCl$_2$, 0.4 mM MgSO$_4$, 0.3 mM KH$_2$PO$_4$, 0.3 mM Na$_2$HPO$_4$, 5.6 mM glucose) plus 20 mM HEPES pH 7.4, 0.05% BSA and 2.5 mM probenicid (50 μl/well) for 1 hour in 5% CO$_2$ at 37° C. After excess dye was discarded, cells were washed in assay buffer and layered with a final volume equal to 45 μl/well (or 30 ul/well for antagonist assay). In the case of antagonist evaluation, antagonist or vehicle was added at this point as a 15 μl aliquot in 4% DMSO-containing buffer at 4× the final concentration (final DMSO=1%), followed by a 20 min incubation. Basal fluorescence was monitored in a fluorometric imaging plate reader or FLIPR™ from Molecular Devices (Sunnyvale, Calif.) with an excitation wavelength of 488 nm and an emission range of 500 to 560 nm. Laser excitation energy was adjusted so that basal fluorescence readings were approximately 8,000 relative fluorescent units (RFU). Cells were then stimulated at room temperature with agonists diluted in assay buffer (15 μl), and RFU were measured at 1.5 second intervals over a period of 2.5 min. Maximum change in fluorescence was calculated for each well. Concentration-response curves derived from the maximum change in fluorescence were analyzed by nonlinear regression (Hill equation). For antagonistic determinations, after 20 min of compound incubation (as above), fixed concentrations of standard agonist serotonin were added.

Example 2E

Increase in Dopamine

Figure 23:
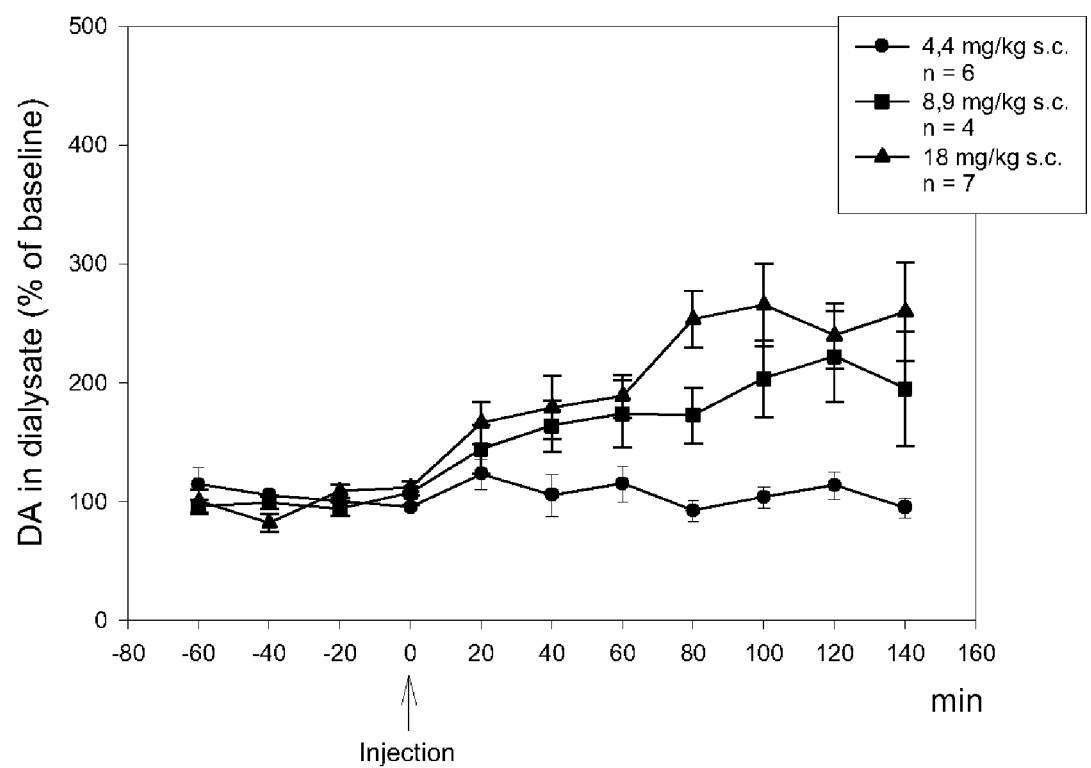

A single injection of compounds of the present invention dose-dependently increased extracellular DA levels in the rat frontal cortex. The compound of the present invention at 8.9 mg/kg and 18 mg/kg s.c., enhanced the DA levels by approximately 100% and 150%, respectively, above baseline levels as depicted in FIG. 23. Amounts are calculated as the free base.

Method.

Male Sprague-Dawley rats, initially weighing 275-300 g, were used. The animals were housed under a 12-hr light/dark cycle under controlled conditions for regular indoor temperature (21±2° C.) and humidity (55±5%) with food and tap water available ad libitum. For the three-day treatment experiments osmotic minipumps (Alzet, 2ML1) were used. The pumps were filled under aseptic conditions and implanted subcutaneously under sevoflurance anaesthesia. The experiments were carried out with the minipumps on board. Blood samples for measuring plasma levels of the test compound after 3 days of treatment were collected at the end of the experiments.

Surgery and Microdialysis Experiments.

Animals were anaesthetised with hypnorm/dormicum (2 ml/kg) and intracerebral guide cannulas (CMA/12) were stereotaxically implanted into the hippocampus, positioning the dialysis probe tip in the ventral hippocampus (co-ordinates: 5.6 mm anterior to bregma, lateral −5.0 mm, 7.0 mm ventral to dura or in the frontal cortex (co-ordinates: 3.2 mm anterior to bregma; lateral, 3.0 mm; 40 mm ventral to dura). Anchor screws and acrylic cement were sued for fixation of the guide cannulas. The body temperature of the animals was monitored by rectal probe and maintained at 37° C. The rats were allowed to recover from surgery for 2 days, housed singly in cages. On the day of the experiment a microdialysis probe (CMA/12, 0,5 mm diameter, 3 mm length) was inserted through the guide cannula. The probes were connected via a dual channel swivel to a microinjection pump. Perfusion of the microdialysis probe with filtered Ringer solution (145 mm NaCl, 3 mM KCl, 1 mM $MgCl_2$, 1.2 mM $CaCl_2$) was begun shortly before insertion of the probe into the brain and continued for the duration of the experiment at a constant flow rate of 1 (1,3) μL/min. After 180 min of stabilisation, the experiments were initiated. Dialysates were collected every 20 (30) min.

After the experiments the rats were sacrificed by decapitation, their brains removed, frozen and sliced for probe placement verification.

Analysis of Dialysates.

Concentration of dopamine in the dialysates was analysed by means of HPLC with electrochemical detection. The monoamines were separated by reverse phase liquid chromatography (ODS 150×3 mm, 3 μM). Dopamine: Mobile phase consisting of 90 mM $NaH_2PO_4$, 50 mM sodium citrate, 367 mg/l sodium 1-octanesulfonic acid, 50 μM EDTA and 8% acetonitrile (pH 4.0) at a flow rate of 0.5 ml/min. Electrochemical detection was accomplished using a coulometric detector; potential set at 250 mV (guard cell at 350 mV) (Coulochem II, ESA).

Example 2F

Increase in Acetylcholin

The experiment was designed to evaluate the effects of compounds of the present invention on extracellular levels of acetylcholine in the prefrontal cortex of freely-moving rats.

Male Wistar rats (280-350 g; Harlan, Zeist, The Netherlands) were used for the experiments. Rats were individually housed in plastic cages (30×30×40 cm) and had ad libitum access to food and water.

Rats were anesthetized using isoflurane (2%, 400 mL/min $N_2O$, 400 ml/min $O_2$). Lidocaine (10% m/v) was used for local anesthesia. Each animal was placed into a stereotaxic frame (Kopf instruments, USA), and home-made I-shaped probes (Hospal AN 69 membrane, 4 mm exposed surface) were inserted into the medial prefrontal cortex (mPFC) using the rat brain atlas of Paxinos and Watson (1982). Coordinates for the tip of the probe was mPFC [AP=3.4 mm, L=−0.8 mm, V=5.0 mm]. The probe was then fixed to the skull with dental cement and a screw. Flunixin (1 mg/kg s.c.) was administered as post-operative analgesic.

Experiments were carried out 24-48 hours after surgery. On the day of the experiment, rats were connected with flexible PEEK tubing to microperfusion pumps (CMA 102), and the dialysis probes were perfused with a Ringer buffer containing 147 mM NaCl, 3.0 mM KCl, 1.2 mM $CaCl_2$, and 1.2 mM $MgCl_2$, at a flow rate of 1.5 μL/min. Microdialysis samples were collected at 30 min intervals into mini-vials containing 55 μL 0.02 M formic acid for determination of acetylcholine. Samples were collected by an automated fraction collector (CMA 142), and stored at −80° C. until analyzed. After completion of the experiments the rats were sacrificed. The brains were removed and cured in paraformaldehyde solution (4% m/v). The positioning of each probe was verified histologically according to Paxinos and Watson (1982), by making coronal sections of the brain.

The test compound was dissolved in 10% 2-OH-propyl-beta-cyclodextrin and administration occurred by subcutaneous injections of 5 mL/kg volumes in different doses.

Concentrations of acetylcholine were determined by HPLC with tandem mass spectrometry (MS/MS) detection.

Aliquots (25 μL) were injected onto the HPLC column by an automated sample injector (PerkinElmer Instruments, series 200). Chromatographic separation was performed on a reverse-phase 150×2.00 mm (4 μm) analytical column (Phenomenex Synergy MAX-RP, Bester) protected by a 4×2.0 mm guard column (Phenomenex Synergy MAX-RP AJO-6073, Bester), both held at a temperature of 30° C. The mobile phase (isocratic) consisted of ultrapurified water (UP), acetonitrile (ACN), and trifluoroacetic acid (TFA) (UP:ACN:TFA=95.0:0.5:0.1 v/v/v %). Mobile phase was run through the system at a flow rate of 0.300 mL/min by an HPLC pump (PerkinElmer Instruments, series 200 micro pump).

The LC/MS analyses were performed using a API 4000 MS/MS system consisting of a API 4000 MS/MS detector and a Turbo Ion Spray interface (both from Applied Biosystems, the Netherlands). The acquisitions were performed in positive ionization mode, with ion spray voltage set at 5.5 kV, the nebulizer gas pressure at 50 psig (on a SCIEX scale 0-90) with a probe temperature of 600° C. The instrument was operated in multiple-reaction-monitoring (MRM) mode for detection of acetylcholine (precursor 146.1 Da, product 86.8 Da). The collision energy was 21.0 eV, and the collision gas (nitrogen) pressure was held at 7 (on a SCIEX scale of 0-12). Data were calibrated and quantitated using the Analyst™ data system (Applied Biosystem, version 1.2).

Two consecutive microdialysis samples with less then 50% variation were taken as baseline levels and set at 100%. Changes in acetylcholine concentration were expressed as percent of baseline within the same subject.

The data are shown in FIG. 24

Example 2G

Increase in Acetylcholine

The experiment was designed to evaluate the effects of compounds of the present invention on extracellular levels of acetylcholine in the prefrontal cortex and ventral hippocampus of freely-moving rats.

Male Sprague-Dawley rats, initially weighing 275-300 g, were used. The animals were housed under a 12-hr light/dark cycle under controlled conditions for regular indoor temperature (21±2° C.) and humidity (55±5%) with food and tap water available ad libitum.

Surgery and Microdialysis Experiments

Rats were anaesthetised with hypnorm/dormicum (2 ml/kg) and intracerebral guide cannulas (CMA/12) were stereotaxically implanted into the hippocampus, aiming to position the dialysis probe tip in the ventral hippocampus (co-ordinates: 5.6 mm posterior to bregma, lateral −5.0 mm, 7.0 mm ventral to dura or in the frontal cortex (co-ordinates: 3.2 mm anterior to bregma; lateral, 0.8 mm; 4.0 mm ventral to dura). Anchor screws and acrylic cement were used for fixation of the guide cannulas. The body temperature of the animals was monitored by rectal probe and maintained at 37° C. The rats were allowed to recover from surgery for 2 days, housed singly in cages. On the day of the experiment a microdialysis probe (CMA/12, 0,5 mm diameter, 3 mm length) was inserted through the guide cannula.

The probes were connected via a dual channel swivel to a microinjection pump. Perfusion of the microdialysis probe with filtered Ringer solution (145 mm NaCl, 3 mM KCl, 1 mM $MgCl_2$, 1.2 mM $CaCl_2$ containing 0.5 µM neostigmine) was begun shortly before insertion of the probe into the brain and continued for the duration of the experiment at a constant flow rate of 1 µl/min. After 180 min of stabilisation, the experiments were initiated. Dialysates were collected every 20 min. After the experiments the animals were sacrificed, their brains removed, frozen and sliced for probe placement verification.

Analysis of Dialysate Acetylcholine

Concentration of acetylcholine (ACh) in the dialysates was analysed by means of HPLC with electrochemical detection using a mobile phase consisting of 100 mM disodium hydrogenphosphate, 2.0 mM octane sulfonic acid, 0.5 mM tetramethyl-ammonium chloride and 0.005% MB (ESA), pH 8.0. A pre-column enzyme reactor (ESA) containing immobilised choline oxidase eliminated choline from the injected sample (10 µl) prior to separation of ACh on the analytical column (ESA ACH-250); flow rate 0.35 ml/min, temperature: 35° C. After the analytical column the sample passed through a post-column solid phase reactor (ESA) containing immobilised acetylcholinesterase and choline oxidase. The latter reactor converted ACh to choline and subsequently choline to betaine and $H_2O_2$. The latter was detected electrochemical by using a platinum electrode (Analytical cell: ESA, model 5040).

Data Presentation

Figure 25B:
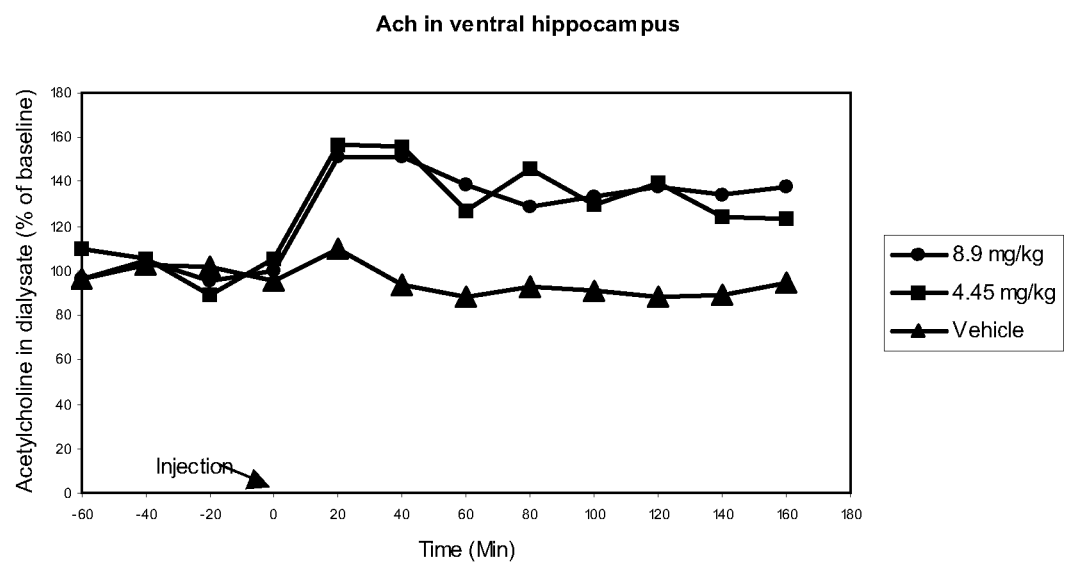

In single injection experiments the mean value of 3 consecutive ACh samples immediately preceding compound administration served as the basal level for each experiment and data were converted to percentage of basal (mean basal pre-injection values normalized to 100%). The data are presented in FIGS. 25a and 25b.

The data presented in FIG. 24 show unexpected drops in the acetylcholine levels (see e.g. 8 mg/kg) which are difficult to explain and which are ascribed to experimental uncertainty. Overall, both data sets from example 2F and 2G show the same, i.e. a dose dependent increase in the extra-cellular acetylcholine levels in the brain. This pre-clinical finding is expected to translate into an improvement in cognition in a clinical setting useful e.g. in the treatment of diseases characterised by a cognitive impairment, such as e.g. Alzheimer's patients, partial responders, cognitive impairment etc.

Example 3

Effect on Neuropathic Pain

To demonstrate an efficacy against neuropathic pain, the compound of the present invention was tested in the formalin model of neuropathic pain [*Neuropharm.*, 48, 252-263, 2005; *Pain*, 51, 5-17, 1992]. In this model, mice receive an injection of formalin (4.5%, 20 µl) into the plantar surface of the left hind paw and afterwards are placed into individual glass beakers (2 l capacity) for observation. The irritation caused by the formalin injection elicits a characteristic biphasic behavioural response, as quantified by the amount of time spent licking the injured paw. The first phase (~0-10 minutes) represents direct chemical irritation and nociception, whereas the second (~20-30 minutes) is thought to represent pain of neuropathic origin. The two phases are separated by a quiescent period in which behaviour returns to normal. Measuring the amount of time spent licking the injured paw in the two phases assesses the effectiveness of test compounds to reduce the painful stimuli.

Eight C57/B6 mice (ca. 25 g) were tested per group. Table 4 below show the amount of time spent licking the injured paw in the two phases, i.e. 0-5 minutes and 20-30 minutes post formalin injection. The amount of compound administered is calculated as the free base.

TABLE 4

|  | Vehicle | 1.0 mg/kg | 2.5 mg/kg | 10 mg/kg |
| --- | --- | --- | --- | --- |
| 0-5 minutes (sec) | 42 | 37 | 30 | 37 |
| 20-30 minutes (sec) | 41 | 43 | 26 | 6 |

The data in table 4 shows that the compound of the present invention has little effect in the first phase representing direct chemical irritation and nociception. More notably, the data also show a clear and dose dependent decrease in the time spent licking paws in the second phase indicating an effect of the compound of the present invention in the treatment of neuropathic pain.

Example 4

Capsules

4-[2-(4-methylphenylsulfanyl)-phenyl]piperidine hydrobromide was mixed with microcrystalline cellulose in a first step. In a second step magnesium stearate was mixed in. Capsules with four strengths were prepared—the active ingredient is stated as the free base

|  | 1 mg | 5 mg | 25 mg |
| --- | --- | --- | --- |
| Active ingredient | 12.85 g | 64.25 g | 321.25 g |
| Microcrystalline cellulose | 2026.55 g | 2034.55 g | 1846.85 g |
| Magnesium stearate | 20.6 g | 21.2 g | 21.9 g |
| Weight of capsule content | 206 mg | 212 mg | 219 mg |

10.000 capsules were prepared from each batch.

The invention claimed is:
1. Compound I, which is 4-[2-(4-methylphenyl-sulfanyl)phenyl]piperidine

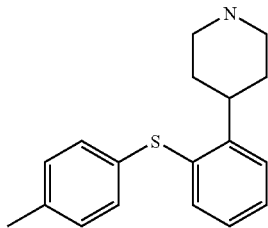

and pharmaceutically acceptable salts thereof in a crystalline form selected from the group consisting of an:
HBr addition salt in a crystalline form characterized by peaks in an XRPD at 6.08, 14.81, 19.26 and 25.38+/−0.10° 2θ;
DL-lactic acid addition salt in a crystalline form characterized by peaks in an XRPD at 5.30, 8.18, 9.44 and 17.24+/−0.10° 2θ;
glutaric acid addition salt (1:1) in a crystalline form characterized by peaks in an XRPD at 9.39, 11.70, 14.05 and 14.58+/−0.10° 2θ; and
glutamic acid addition salt (1:1) in a crystalline form characterized by peaks in an XRPD at 7.71, 14.01, 19.26 and 22.57+/−0.10° 2θ.

2. The compound according to claim 1, which compound is the HBr addition salt in a crystalline form characterized by peaks in an XRPD at 6.08, 14.81, 19.26 and 25.38+/−0.10° 2θ.

3. The compound according to claim 2, wherein said crystalline form is characterised by an XRPD as depicted in FIG. 1.

4. The compound according to claim 1, which compound is the DL-lactic acid addition salt in a crystalline form characterized by peaks in an XRPD at 5.30, 8.18, 9.44 and 17.24+/−0.10° 2θ.

5. The compound according to claim 4, wherein said crystalline form is characterised by an XRPD as depicted in FIG. 4.

6. The compound according to claim 1, which compound is the glutaric acid addition salt (1:1) in a crystalline form characterized by peaks in an XRPD at 9.39, 11.70, 14.05 and 14.58+/−0.10° 2θ.

7. The compound according to claim 6, wherein said crystalline form is characterised by an XRPD as depicted in FIG. 8.

8. The compound according to claim 1, which compound is the glutamic acid addition salt (1:1) in a crystalline form characterized by peaks in an XRPD at 7.71, 14.01, 19.26 and 22.57+/−0.10° 2θ.

9. A pharmaceutical composition comprising a compound according to claim 1 together with a pharmaceutically acceptable excipient.

10. A method for the therapeutic treatment of a disease selected from chronic pain, depression in partial responders, treatment resistant depression, Alzheimer's disease, cognitive impairment, ADHD, melancholia, PTSD, hot flushes, sleep apnea, alcohol, nicotine or carbohydrate craving, substance abuse, alcohol or drug abuse, emesis, eating disorders, IBS, affective disorders, depression, major depressive disorder, postnatal depression, depression associated with bipolar disorder, Alzheimer's disease, psychosis or Parkinson's disease, anxiety, general anxiety disorder, social anxiety disorder, obsessive compulsive disorder, panic disorder, panic attacks, phobia, social phobia, agoraphobia or stress urinary incontinence, the method comprising administering to a patient in need thereof a therapeutically effective amount of a compound according claim 1.

11. The method according to claim 10, wherein said disease is chronic pain.

12. The method according to claim 11, wherein said chronic pain is selected from phantom limb pain, neuropathic pain, diabetic neuropathy, post-herpetic neuralgia (PHN), carpal tunnel syndrome (CTS), HIV neuropathy, complex regional pain syndrome (CPRS), trigeminal neuralgia/trigeminus neuralgia/tic douloureux, surgical intervention (e.g. post-operative analgesics), diabetic vasculopathy, capillary resistance or diabetic symptoms associated with insulitis, pain associated with angina, pain associated with menstruation, pain associated with cancer, dental pain, headache, migraine, tension-type headache, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain and geriatric pain.

13. The method according to claim 12, wherein said chronic pain is neuropathic pain.

14. The method according to claim 13, wherein said neuropathic pain is selected from hyperpathia, hyperalgesia, neuropathy, diabetic neuropathy, neuritis, neuralgia, hyperesthesia, causalgia, and allodynia.

15. The method of claim 10, wherein said compound is the HBr addition salt in a crystalline form characterized by peaks in an XRPD at 6.08, 14.81, 19.26 and 25.38+/−0.10° 2θ.

16. The method of claim 10, wherein said compound is the DL-lactic acid addition salt in a crystalline form characterized by peaks in an XRPD at 5.30, 8.18, 9.44 and 17.24+/−0.10° 2θ.

17. The method of claim 10, wherein said compound is the glutaric acid addition salt (1:1) in a crystalline form characterized by peaks in an XRPD at 9.39, 11.70, 14.05 and 14.58+/−0.10° 2θ.

18. The method of claim 10, wherein said compound is the glutamic acid addition salt (1:1) in a crystalline form characterized by peaks in an XRPD at 7.71, 14.01, 19.26 and 22.57+/−0.10° 2θ.

* * * * *